United States Patent
Magnuson et al.

(10) Patent No.: US 8,191,220 B2
(45) Date of Patent: Jun. 5, 2012

(54) METHOD FOR LOADING A MEDICAL DEVICE INTO A DELIVERY SYSTEM

(75) Inventors: Mark A. Magnuson, Bloomington, IN (US); Fred T. Parker, Unionville, IN (US); Palle M. Hansen, Bjaeverskov (DK)

(73) Assignee: Cook Medical Technologies LLC, Bloomington, IN (US)

( * ) Notice: Subject to any disclaimer, the term of this patent is extended or adjusted under 35 U.S.C. 154(b) by 1217 days.

(21) Appl. No.: 11/950,244

(22) Filed: Dec. 4, 2007

(65) Prior Publication Data

US 2008/0215131 A1 Sep. 4, 2008

Related U.S. Application Data

(60) Provisional application No. 60/872,692, filed on Dec. 4, 2007.

(51) Int. Cl.
B23P 11/02 (2006.01)
A61F 2/06 (2006.01)
C22F 1/10 (2006.01)

(52) U.S. Cl. ......... 29/405; 148/563; 148/402; 623/1.18; 623/1.19; 29/447

(58) Field of Classification Search ............... 29/405, 29/447; 148/563, 402; 623/1.18, 1.19
See application file for complete search history.

(56) References Cited

U.S. PATENT DOCUMENTS

| | | |
|---|---|---|
| 4,435,229 A | 3/1984 | Johnson |
| 4,503,569 A | 3/1985 | Dotter |
| 4,580,568 A | 4/1986 | Gianturco |
| 4,655,771 A | 4/1987 | Wallstén |
| 4,665,906 A | 5/1987 | Jervis |
| 4,681,110 A | 7/1987 | Wiktor |
| 4,707,196 A | 11/1987 | Honma et al. |
| 4,743,251 A | 5/1988 | Barra |
| 4,753,689 A | 6/1988 | Rizzo et al. |
| 4,795,458 A | 1/1989 | Regan |

(Continued)

FOREIGN PATENT DOCUMENTS

EP 0411118 A1 2/1991

(Continued)

OTHER PUBLICATIONS

Bataillard, L.; Bidaux, J.E.; Gotthardt, R. "Interaction Between Microstructure and Multiple-Step Transformation in Binary NiTi Alloys Using in-situ Transmission Electron Microscopy Observations," *Philosophical Magazine A*, 1998, 78(2), pp. 327-344.

(Continued)

*Primary Examiner* — Jermie Cozart
(74) *Attorney, Agent, or Firm* — Brinks Hofer Gilson & Lione

(57) ABSTRACT

A process to load a medical device comprising a shape memory material into a delivery system is described herein. According to one aspect, the method includes applying a force to the medical device to obtain a delivery configuration thereof, where the device is at a first temperature within an R-phase temperature range of the shape memory material during application of the force. The medical device is cooled in the delivery configuration to a second temperature at or below a martensite finish temperature of the shape memory material. The force is then removed from the medical device, and the device is loaded into a delivery system. Preferably, the medical device substantially maintains the delivery configuration during the loading process.

21 Claims, 7 Drawing Sheets

U.S. PATENT DOCUMENTS

| | | | |
|---|---|---|---|
| 4,881,981 | A | 11/1989 | Thoma et al. |
| 4,935,068 | A | 6/1990 | Duerig |
| 4,954,126 | A | 9/1990 | Wallstén |
| 4,984,581 | A | 1/1991 | Stice |
| 5,037,427 | A | 8/1991 | Harada et al. |
| 5,061,275 | A | 10/1991 | Wallstén et al. |
| 5,067,957 | A | 11/1991 | Jervis |
| 5,147,370 | A | 9/1992 | McNamara et al. |
| 5,190,546 | A | 3/1993 | Jervis |
| 5,197,978 | A | 3/1993 | Hess |
| 5,201,901 | A | 4/1993 | Harada et al. |
| 5,226,913 | A | 7/1993 | Pinchuk |
| 5,354,309 | A | 10/1994 | Schnepp-Pesch et al. |
| 5,395,390 | A | 3/1995 | Simon et al. |
| 5,405,377 | A | 4/1995 | Cragg |
| 5,466,242 | A | 11/1995 | Mori |
| 5,534,007 | A | 7/1996 | St. Germain et al. |
| 5,540,712 | A | 7/1996 | Kleshinski et al. |
| 5,540,713 | A | 7/1996 | Schnepp-Pesch et al. |
| 5,545,210 | A | 8/1996 | Hess et al. |
| 5,554,181 | A | 9/1996 | Das |
| 5,562,641 | A | 10/1996 | Flomenblit et al. |
| 5,562,725 | A | 10/1996 | Schmitt et al. |
| 5,562,728 | A | 10/1996 | Lazarus et al. |
| 5,575,818 | A | 11/1996 | Pinchuk |
| 5,597,378 | A | 1/1997 | Jervis |
| 5,601,593 | A | 2/1997 | Freitag |
| 5,624,508 | A | 4/1997 | Flomenblit et al. |
| 5,630,840 | A | 5/1997 | Mayer |
| 5,636,641 | A | 6/1997 | Fariabi |
| 5,674,277 | A | 10/1997 | Freitag |
| 5,718,159 | A | 2/1998 | Thompson |
| 5,741,333 | A | 4/1998 | Frid |
| 5,758,562 | A | 6/1998 | Thompson |
| 5,782,741 | A | 7/1998 | Bradshaw et al. |
| 5,830,179 | A | 11/1998 | Mikus et al. |
| 5,836,066 | A | 11/1998 | Ingram |
| 5,840,387 | A | 11/1998 | Berlowitz-Tarrant et al. |
| 5,843,119 | A | 12/1998 | Shmulewitz |
| 5,846,247 | A | 12/1998 | Unsworth et al. |
| 5,851,217 | A | 12/1998 | Wolff et al. |
| 5,876,434 | A | 3/1999 | Flomenblit et al. |
| 5,882,444 | A | 3/1999 | Flomenblit et al. |
| 5,888,201 | A | 3/1999 | Stinson et al. |
| 5,928,217 | A | 7/1999 | Mikus et al. |
| 5,964,770 | A | 10/1999 | Flomenblit et al. |
| 6,042,605 | A | 3/2000 | Martin et al. |
| 6,042,606 | A | 3/2000 | Frantzen |
| 6,051,021 | A | 4/2000 | Frid |
| 6,139,536 | A | 10/2000 | Mikus et al. |
| 6,306,141 | B1 | 10/2001 | Jervis |
| 6,402,765 | B1 | 6/2002 | Monassevitch et al. |
| 6,416,544 | B2 | 7/2002 | Sugita et al. |
| 6,416,545 | B1 | 7/2002 | Mikus et al. |
| 6,540,849 | B2 | 4/2003 | DiCarlo et al. |
| 6,569,183 | B1 | 5/2003 | Kim et al. |
| 6,572,646 | B1 | 6/2003 | Boylan et al. |
| 6,626,937 | B1 | 9/2003 | Cox |
| 6,656,201 | B2 | 12/2003 | Ferrera et al. |
| 6,666,881 | B1 | 12/2003 | Richter et al. |
| 6,776,795 | B2 | 8/2004 | Pelton |
| 6,783,438 | B2 | 8/2004 | Aloise et al. |
| 6,896,684 | B2 | 5/2005 | Monassevitch et al. |
| 6,899,730 | B1 | 5/2005 | Rivelli, Jr. |
| 7,033,386 | B2 | 4/2006 | Richter et al. |
| 2002/0151967 | A1 | 10/2002 | Mikus et al. |
| 2002/0177899 | A1 | 11/2002 | Eum et al. |
| 2003/0018343 | A1 | 1/2003 | Mathis |
| 2003/0199920 | A1 | 10/2003 | Boylan et al. |
| 2004/0260377 | A1 | 12/2004 | Flomenblit et al. |
| 2005/0043757 | A1 | 2/2005 | Arad et al. |
| 2005/0154450 | A1 | 7/2005 | Larson et al. |
| 2005/0187612 | A1 | 8/2005 | Edwin |
| 2005/0198777 | A1 | 9/2005 | Mabe |
| 2007/0079494 | A1 | 4/2007 | Serrano |

FOREIGN PATENT DOCUMENTS

| | | |
|---|---|---|
| EP | 1205743 A1 | 5/2002 |
| EP | 0744164 B1 | 9/2003 |
| EP | 1354566 A2 | 10/2003 |
| JP | 59-113165 | 6/1984 |
| WO | WO 92/19310 | 11/1992 |
| WO | WO 95/30385 | 11/1995 |
| WO | WO 95/31945 | 11/1995 |
| WO | WO 97/13475 | 4/1997 |
| WO | WO 97/21403 | 6/1997 |
| WO | WO 00/04846 | 2/2000 |
| WO | WO 2006/086709 A1 | 8/2006 |

OTHER PUBLICATIONS

Batalu, D.; Guoqiu, H.; Aloman, A.; Xiaoshan, L.; Zhihua, Z. "Determination of Some Mechanical Properties of TiNi (50.6 at.% Ni) Shape Memory Alloy Using Dynamic Mechanical Analysis and Tensile Tests," *Journal of Optoelectronics and Advanced Materials*, 2006, 8(2), pp. 694-698.

Besseghini, S.; Villa, E.; Passaretti, F.; Carcano, G. "Two Way Shape Memory Training in NiTi Shape Memory Alloys," *Presentation at E-MRS Fall Meeting 2005, Symposium C*, 2005, http://www.science24.com/paper/3739, 1 page.

Cai, W.; Lu, X.L.; Zhao, L.C. "Damping Behavior of TiNi-Based Shape Memory Alloys," Materials Science and Engineering A, 2005, 394, pp. 78-82.

Carballo, M.; Pu, Z.J.; Wu, K.H. "Variation of Electrical Resistance and the Elastic Modulus of Shape Memory Alloys Under Different Loading and Temperature Conditions," *Journal of Intelligent Material Systems and Structures*, 1995, 6, pp. 557-565.

Chang, C-Y.; Vokoun, D.; Hu, C-T. "Two-Way Shape Memory Effect of NiTi Alloy Induced by Constraint Aging Treatment at Room Temperature," *Metallurgical and Materials Transactions A*, 2001, 32A, p. 1629.

Duerig, T.W. "Some Unsolved Aspects of Nitinol," *Materials Science and Engineering A*, 2006, 438-440, pp. 69-74.

Duerig, T. "Puzzler 2," *The SMST Newsletter*, 2006, 2 pages.

Duerig, T.; Tolomeo, D.E.; Wholey, M. "An Overview of Superelastic Stent Design," *Min Invas Ther & Allied Technol*, 2000, 9(3/4), pp. 235-246.

Hwang, C.M.; Meichle, M.; Salamon, M.B.; Wayman, C.M. "Transformation Behaviour of a $Ti_{50}Ni_{47}Fe_3$ Alloy I. Premartensitic Phenomena and the Incommensurate Phase," *Philosophical Magazine A*, 1983, 47(1), 9-30.

Hwang, C.M.; Meichle, M.; Salamon, M.B.; Wayman, C.M. "Transformation Behaviour of a $Ti_{50}Ni_{47}Fe_3$ Alloy II. Subsequent Premartensitic Behaviour and the Commensurate Phase," *Philosophical Magazine A*, 1983, 47(1), 31-62.

Khachin, V.N.; Gjunter, V.E.; Sivokha, V.P.; Savvinov, A.S. "Lattice Instability, Martensitic Transformations, Plasticity and Anelasticity of TiNi," *Proc. ICOMAT*, 1979, 79, pp. 474-479.

Khalil-Allafi, J.; Eggeler, G.; Schmahl W.W.; Sheptyakov, D. "Quantitative Phase Analysis in Microstructures Which Display Multiple Step Martensitic Transformations in Ni-rich NiTi Shape Memory Alloys," *Materials Science and Engineering A*, 2006, 438-440, pp. 593-596.

Mazzolai, F.M.; Biscarini, A.; Coluzzi, B.; Mazzolai, G.; Villa, E.; Tuissi, A. "Low-Frequency Internal Friction of Hydrogen-Free and Hydrogen-Doped NiTi Alloys," *Acta Materialia*, 2007, 55, pp. 4243-4252.

Mehta, A.; Gong, X-Y.; Imbeni, V.; Pelton, A.R.; Ritchie, R.O. "Understanding the Deformation and Fracture of Nitinol Endovascular Stents Using In Situ Synchrotron X-Ray Microdiffraction," *Advanced Materials*, 2007, 19, pp. 1183-1186.

Mehta, A.; Imbeni, V.; Ritchie, R.O.; Duerig, T.W. "On the Electronic and Mechanical Instabilities in $Ni_{50.9}Ti_{49.1}$," *Materials Science and Engineering A*, 2004, 378, pp. 130-137.

Michutta, J.; Somsen, Ch.; Yawny, A.; Dlouhy, A.; Eggeler, G. "Elementary Martensitic Transformation Processes in Ni-rich NiTi Single Crystals with $Ni_4Ti_3$ Precipitates," *Acta Materialia*, 2006, 54, pp. 3525-3542.

Mihálcz, I. "Fundamental Characteristics and Design Method for Nickel-Titanium Shape Memory Alloy," *Periodica Polytechnica Ser. Mech. Eng.*, 2001, 45(1), pp. 75-86.

Miyazaki, S.; Otsuka, K. "Mechanical Behaviour Associated with the Premartensitic Rhombohedral-Phase Transition in a $Ti_{50}Ni_{47}Fe_3$ Alloy," *Philosophical Magazines A*, 1984, 50(3), pp. 393-408.

Miyazaki, S.; Otsuka, K.; Wayman, C.M. "The Shape Memory Mechanism Associated with the Martensitic Transformation in Ti-Ni Alloys—II. Variant Coalescence and Shape Recovery," *Acta Metall.*, 1989, 37(7), pp. 1885-1890.

Miyazaki, S;. Wayman, C.M. "The R-Phase Transition and Associated Shape Memory Mechanism in Ti-Ni Single Crystals," *Acta metall.*, 1988, 36(1), pp. 181-192.

Ng, K.L.; Sun, Q.P. "Stress-Induced Phase Transformation and Detwinning in NiTi Polycrystalline Shape Memory Alloy Tubes," *Mechanics of Materials*, 2006, 38, pp. 41-56.

Schmahl, W.; Bochum, R.U. "Crystal Structure Determination of $Ni_4Ti_4$ Precipitates and R-Phase in SM Alloys," *BENSC Experimental Report*, 2003, 1 page.

Šittner, P.; Landa, M.; Lukáš, P.; Novák, V. "R-Phase Transformation Phenomena in Thermomechanically Loaded NiTi Polycrystals," *Mechanics of Materials*, 2006, 38, pp. 475-492.

Šittner, P.; Landa, M.; Sedlák, P.; Lukáš, P.; Novák, V. "On the Role of the R-Phase in Thermomechanical Behaviors of Commercial NiTi Wires," *Proceedings of the International Conference on Shape Memory and Superelastic Techologies*, Oct. 3-7, 2004 in Baden-Baden, Germany, ASM International, Materials Park, OH, 2006, pp. 29-36.

Šittner, P.; Lukáš, P.; Neov, D.; Lugovyy, D. "Martensitic Transformations in NiTi Polycrystals Investigated by In-Situ Neutron Diffraction," *Materials Science Forum*, 2003, 426-432, pp. 2315-2320.

Tobushi, H.; Yamada, S.; Hachisuka, T.; Ikai, A.; Tanaka, K. "Thermomechanical Properties Due to Martensitic and R-Phase Transformations of TiNi Shape Memory Alloy Subjected to Cyclic Loadings," *Smart Mater. Struct.*, 1996, 5, pp. 788-795.

Tsoi, K.A. "Thermomechanical and Transformational Behaviour and Applications of Shape Memory Alloys and their Composites," *A Thesis Submitted for the Degree of Doctor of Philosophy at the School of Aerospace, Mechanical and Mechatronic Engineering University of Sydney*, 2002, Chapter 1, pp. 1-16 (17 pages with title page).

Uchil, J.; Mahesh, K.K.; Ganesh Kumara, K. "Electrical Resistivity and Strain Recovery Studies on the Effect of Thermal Cycling Under Constant Stress on R-phase in NiTi Shape Memory Alloy," *Physica B*, 2002, 324, pp. 419-428.

Wu, K.; Dalip, S.K.; Liu, Y.; Pu, Z. "Damping Characteristics of R-Phase NiTi Shape Memory Alloys," *SPIE*, 1995, 2441, pp. 139-148.

International Search Report and the Written Opinion for International Patent Application No. PCT/US2007/024932 dated May 8, 2008.

"Nitinol FAQ," *Memry Corporation*, 2006, 6 pages.

"Setting Shapes in NiTi," *Johnson Matthey*, (printed from website) 2006, 1 page.

"Shape Memory Alloy," *Wikipedia, the Free Encyclopedia*, (printed from website) 2006, 4 pages.

"Standard Terminology for Nickel-Titanium Shape Memory Alloys," *American Society for Testing and Materials (ASTM) Standard F2005-05*, ASTM International, West Conshohocken, PA, 3 pages.

"Standard Test Method for Transformation Temperature of Nickel-Titanium Alloys by Thermal Analysis," *American Society for Testing and Materials (ASTM) Standard F2004-05*, ASTM International, West Conshohocken, PA, 2005, 4 pages.

"Transformation Temperature Hysteresis in NiTi Alloys," *Johnson Matthey*, (printed from website) 2006, 2 pages.

"Using Nitinol Alloys," *Johnson Matthey Engineering Reference*, 2004, 65 pages.

Besseghini, S.; Villa, E.; Portman, J. "DMA Characterization of a Ni50.5at%Ti Shape Memory Alloys," *Int. J. Appl. Electr. and Mech.*, 2006, 23, pp. 33-38.

Cha, S-Y.; Jeong, S-Y.; Park, J.H.; Park, S.E.; Park, J.K.; Cho, C.R. "Thermodynamic and Structural Characterization of High- and Low-Temperature Nitinol," *J. of Korean Phys. Soc.*, 2006, 49, pp. S580-S583.

Eggeler, G.; Khalil-Allafi, J.; Gollerthan, S.; Somsen, C.; Schmahl, W.; Sheptyakov, D. "On the Effect of Aging on Martensitic Transformations in Ni-Rich NiTi Shape Memory Alloys," *Smart Mater. Struct.*, 2005, 14, p. S186-S191.

Funakubo, H. *Shape Memory Alloys*, Gordon and Breach Science Publishers S.A., New York, USA, 1987, pp. 194-200, 267-269.

Hwang, C.M.; Wayman, C.M. "Diffuse Electron Scattering from an Incommensurate Phase in a $Ti_{58.7}Ni_{37.5}Al_{3.8}$ Alloy," *Acta Metallurgica*, 1984, 32(1), pp. 183-187.

Imbeni, V.; Mehta, A.; Robertson, S.W.; Duerig, T.W.; Pelton, A.R; Ritchie, R.O. "On the Mechanical Behavior of Nitinol Under Multiaxial Loading Conditions and InSitu Synchrotron X-Ray," *SMST-2003: Proceedings of the International Conference on Shape Memory and Superelastic Technologies*, edited by A.R. Pelton, T.W. Duerig, SMST Society, Inc., Menlo Park, California, USA, 2004, pp. 267-276.

Khalil-Allafi, J.; Ren, X.; Eggeler, G. "The Mechanism of Multistage Martensitic Transformations in Aged Ni-Rich NiTi Shape Memory Alloys," *Acta. Mater.*, 2002, 50, pp. 793-803.

Kim, J.I.; Liu, Y.; Miyazaki, S. "Ageing-induced Two-Stage R-Phase Transformation in Ti-50.9at.%Ni," *Acta. Mater.*, 2004, 52, pp. 487-499.

Ling, H.C.; Kaplow, R. "Phase Transitions and Shape Memory in NiTi," *Met Trans A*, 1980, 11A, pp. 77-83.

Lukáš, P.; Šittner, P.; Neov, D.; Novák, V.; Lugovyy, D.; Tovar, M. "R-Phase Phenomena in Neutron Diffraction Investigations of Thermomechanically Loaded NiTi Polycrystals," *Mater. Sci. Forum*, 2002, 404-407, pp. 835-840.

Miyazaki, S.; Kimura, S.; Otsuka, K. "Shape-Memory Effect and Pseudoelasticity Associated with the R-Phase Transition in Ti-50•5at.%Ni Single Crystals," *Philos. Mag. A*, 1988, 57(3), pp. 467-478.

Novák, V.; Šittner, P. "Micromechanical Model Simulation of Thermomechanical Behaviors of NiTi Polycrystals Undergoing B2-R-B19' Transformation," *Proceedings of the International Conference on Shape Memory and Superelastic Techologies*, Oct. 3-7, 2004 in Baden-Baden, Germany, ASM International, Materials Park, OH, 2006, pp. 143-149.

Otsuka, K. "Introduction to the R-Phase Transition," *Engineering Aspects of Shape Memory Alloys*, edited by T.W. Duerig, Butterworth-Heinemann, Great Britain, 1990, pp. 36-45.

Otsuka, K.; Ren, X. "Martensitic Transformations in Nonferrous Shape Memory Alloys," *Mater. Sci. Eng. A*, 1999; A273-275, pp. 89-105.

Otsuka, K.; Ren, X. "Physical Metallurgy of Ti-Ni-Based Shape Memory Alloys," *Prog. Mater. Sci.*, 2005, 50, pp. 511-678.

Proft, J.L.; Melton, K.N.; Duerig, T.W. "Yield Drop and Snap Action in a Warm Worked Ni-Ti-Fe Alloy," *ICOMAT-86 (Jap. Inst. of Metals)*, 1986, pp. 742-747.

Saburi, T. "Ti-Ni Shape Memory Alloys," *Shape Memory Materials*, edited by K. Otsuka and C.M. Wayman, Cambridge University Press, New York, USA, 1998, pp. 49-96.

Salamon, M.B.; Meichle, M.E.; Wayman, C.M. "Premartensitic Phases of $Ti_{50}Ni_{47}Fe_3$," *Phys. Rev. B*, 1985, 31(11), pp. 7306-7315.

Schetky, L.M. "Shape Memory Alloys," *Kirk Othmer Encyclopedia of Chemical Technology*, $3^{rd}$ Ed., John Wiley & Sons, Inc., Canada, 1982, vol. 20, pp. 726-736.

Sitepu, H.; Schmahl, W.W.; Allafi, J.K.; Eggeler, G.; Dlouhy, A.; Toebbens, D.M.; Tovar, M. "Neutron Diffraction Phase Analysis During Thermal Cycling of a Ni-Rich NiTi Shape Memory Alloy Using the Rietveld Method," *Scripta Mater.*, 2002, 46, pp. 543-548.

Šittner, P.; Novák, V.; Landa, M.; Lukáš, P. "Deformation Processes in Functional Materials Studied by in situ Neutron Diffraction and Ultrasonic Techniques," *Mater. Sci. Eng. A*, 2007, 462, pp. 12-22.

Šittner, P.; Sedlák, P.; Landa, M.; Novák, V.; Lukáš, P. "In situ Experimental Evidence on R-Phase Related Deformation Processes in Activated NiTi Wires," *Mater. Sci. Eng. A*, 2006, A438-440, pp. 579-584.

Thayer, T.A.; Bagby, M.D.; Moore, R.N.; DeAngelis, R.J. "X-Ray Diffraction of Nitinol Orthodontic Arch Wires," *American Journal of Orthodontics and Dentofacial Orthopedics*, 1995, pp. 604-612.

Todoroki, T.; Tamura, H. "Effect of Heat Treatment After Cold Working on the Phase Transformation in TiNi Alloy," *Trans. Japan Inst. Metals*, 1987, 28(2), pp. 83-94.

Uchil, J.; Mahesh, K.K.; Ganesh Kumara, K. "Calorimetric Study of the Effect of Linear Strain on the Shape Memory Properties of Nitinol," *Physica B*, 2001, 305, pp. 1-9.

Wayman, C.M. "Transformation, Self-Accommodation, Deformation and Shape Memory Behavior of NiTi Alloys," *Shape Memory Materials-Proceedings of the MRS International Meeting on Advanced Materials in 1988*, Materials Research Society, Pittsburgh, USA, 1989, 9, pp. 63-76.

Wayman, C.M.; Cornelis, I.; Shimizu, K. "Transformation Behavior and the Shape Memory in Thermally Cycled TiNi," *Scripta Metall.*, 1972, 6, pp. 115-122.

Zhang, X.; Sehitoglu, H. "Crystallography of the B2 → R → B19' Phase Transformations in NiTi," *Mater. Sci. Eng. A*, 2004, 374, pp. 292-302.

"Standard Test Method for Determination of Transformation Temperature of Nickel-Titanium Shape Memory Alloys by Bend and Free Recovery," *American Society for Testing and Materials (ASTM) Standard F2082-03*, ASTM International, West Conshohocken, PA, 2003. 7 pages.

"Standard Test Method for Determination of Transformation Temperature of Nickel-Titanium Shape Memory Alloys by Bend and Free Recovery," *American Society for Testing and Materials (ASTM) Standard F2082-06*, ASTM International, West Conshohocken, PA, 2006, 7 pages.

METHOD FOR LOADING A MEDICAL DEVICE INTO A DELIVERY SYSTEM

RELATED APPLICATIONS

The present patent document claims the benefit of the filing date under 35 U.S.C. §119(e) of Provisional U.S. Patent Application Ser. No. 60/872,692, filed Dec. 4, 2006, which is hereby incorporated by reference.

The present patent document is related to U.S. patent application Ser. No. 60/992,258, entitled "Method of Characterizing Phase Transformations in Shape Memory Materials," which was filed on Dec. 4, 2007, and is hereby incorporated by reference.

TECHNICAL FIELD

This disclosure is related to a method of preparing an intraluminal medical device for insertion into a body lumen. More particularly, this disclosure is related to a method of loading a medical device into a delivery system.

BACKGROUND

One type of intraluminal medical device that is well-known in the medical profession is a self-expanding stent. Self-expanding stents are often used to treat blockages, occlusions, narrowing ailments and other related problems that restrict flow through body vessels. During delivery to a treatment site in a vessel, a self-expanding stent is typically constrained within a tubular delivery sheath. The sheath prevents the stent from prematurely expanding as it is directed through the vessel to the treatment site. Once in place at the treatment site, the sheath is retracted and the stent deploys automatically to an expanded configuration in which it exerts an outward radial force on the wall of the vessel.

Self-expanding stents are often fabricated from shape memory materials, such as equiatomic or near-equiatomic nickel-titanium alloys (e.g., Nitinol). A shape memory material may undergo a reversible phase transformation that allows it to "remember" and return to a previous shape or configuration. For example, a Nitinol stent may transform from a low-profile compressed configuration during delivery in a vessel to an expanded configuration at a treatment site by transforming from a lower temperature martensitic phase to a higher temperature austenitic phase. The phase transformation may be driven by a change in stress (superelastic effect) or temperature (shape memory effect). In practice, removal of the delivery sheath disposed about the Nitinol stent allows the phase transformation from martensite to austenite to occur at the treatment site. Accordingly, upon removal of the sheath, the Nitinol stent expands from a low-profile compressed configuration to an expanded configuration in support of the vessel. Nitinol may accommodate up to about 7% or 8% recoverable strain $\epsilon_1$, as indicated in FIG. 1A, which shows stress versus strain for a typical Ni—Ti shape memory alloy undergoing a stress-induced transformation between austenite and martensite.

To load a Nitinol stent into a delivery sheath, the stent may be cooled to a temperature at which it has a fully martensitic structure, and then it may be radially compressed to a low profile configuration. Typically, the stent is compressed in a compression apparatus and then removed from the apparatus for loading into the delivery sheath. If the stent is maintained at a temperature below an austenite start temperature ($A_s$) of the shape memory material as it is being removed from the compression apparatus, a phase transformation to austenite and expansion of the stent to its fully expanded configuration may be avoided. However, even if the temperature is sufficiently low to prevent a phase transformation to austenite, the stent may recoil (expand) a small amount $\epsilon_2$ when the compressive stress is removed, as indicated in FIG. 1B, which shows stress versus strain for a typical martensitic Ni—Ti shape memory alloy at a temperature below $A_s$. This recoiling may be sufficient to interfere with the loading process due to the small tolerance between the inner diameter of the delivery sheath and the outer diameter of the compressed stent, both of which are desirably kept as small as possible to minimize the profile of the delivery system. The recoiling stent may thus exert significant radial forces on the inner wall of the sheath during the loading process. Consequently, the stent may buckle or collapse during the loading process instead of sliding smoothly into the sheath. The recoiling of the stent once the force is released and the associated frictional forces during loading may be particularly problematic in the case of longer-length stents.

In view of these problems, the stent loading process may be improved by slowing or preventing the recoiling of the stent upon removal of compressive forces from the stent.

BRIEF SUMMARY

Disclosed herein is a method for loading a medical device into a delivery system. Preferably, the medical device is loaded into the delivery system with minimal frictional forces during loading and without damage to the device. The loading method is applicable to stents and may be particularly advantageous for longer-length stents that may buckle or collapse during conventional loading processes.

According to one aspect, the method includes cooling a stent comprising a shape memory material to an initial temperature at or below a martensite finish temperature of the shape memory material. Prior to the cooling, the stent is preferably at or above an austenite finish temperature of the shape memory material. The stent is then warmed from the initial temperature to a first temperature at or above an R'-phase start temperature and below an austenite start temperature of the shape memory material. A force is applied to the stent at the first temperature to obtain a compressed configuration of the stent. The stent is then cooled in the compressed configuration to a second temperature at or below the martensite finish temperature. After cooling to the second temperature, the force is removed from the stent and the stent is loaded into a delivery system. Preferably, the stent substantially maintains the compressed configuration during loading.

According to one aspect, the method includes applying a force to a medical device comprising a shape memory material to obtain a delivery configuration of the medical device, where the device is at a first temperature above a martensite finish temperature of the shape memory material during application of the force. The medical device is then cooled in the delivery configuration to a second temperature below the first temperature. After cooling, the force is removed from the medical device, and the device is loaded into a delivery system. Preferably, the medical device substantially maintains the delivery configuration during the loading process.

According to another aspect, the method includes applying a force to a medical device comprising a shape memory material to obtain a delivery configuration of the medical device, where the device is at a first temperature within an R-phase temperature range of the shape memory material during application of the force. The force is then removed from the medical device, and the device is loaded into a delivery system.

According to another aspect, the method includes applying a force to a medical device comprising a shape memory material to obtain a delivery configuration of the medical device, where the device is at a first temperature within an R-phase temperature range of the shape memory material during application of the force. The medical device is then cooled in the delivery configuration to a second temperature at or below a martensite finish temperature of the shape memory material. The force is then removed from the medical device, and the device is loaded into a delivery system. Preferably, the medical device substantially maintains the delivery configuration during the loading process.

Also disclosed herein is a training process for a medical device comprising a shape memory material to obtain a secondary shape memory. Above an austenite finish temperature, the medical device has a first configuration. The process includes warming the medical device to a first temperature above a martensite finish temperature of the shape memory material. A force is then applied to the medical device at the first temperature to obtain a second configuration. The medical device is cooled in the second configuration to a second temperature below the first temperature. After the cooling, the force is removed from the medical device. Upon recooling to the second temperature after removing the force, the medical device recovers at least a portion of the second configuration.

DETAILED DESCRIPTION

A method to load a medical device comprising a shape memory material into a delivery system is described. The method may be used to load a self-expanding stent, for example, into a transfer tube, sheath, or other delivery vehicle. By employing the loading method described herein, the medical device may be loaded into the delivery vehicle with minimal frictional forces. The loading method may be particularly advantageous for longer-length medical devices, such as stents, that tend to buckle or collapse during conventional loading processes. Preferably, the shape memory material of the medical device exhibits a two-stage transformation, as discussed below. Also described herein is a method of training a medical device comprising a shape memory material to return to a compressed state upon cooling, thereby exhibiting a two-way shape memory effect.

Phase Transformations in Shape Memory Materials

Nickel-titanium shape memory materials reversibly transform between a lower temperature phase (martensite) and a higher temperature phase (austenite). Austenite is characteristically the stronger phase, and martensite may be deformed up to a recoverable strain of about 8%. Strain introduced in the alloy in the martensitic phase to achieve a shape change may be recovered upon completion of a reverse phase transformation to austenite, allowing the material to return to a previous shape. The forward and reverse phase transformations may be driven by the application and removal of stress (superelastic effect) and/or by a change in temperature (shape memory effect).

As generally understood by those skilled in the art, martensite start temperature ($M_s$) refers to the temperature at which a phase transformation to martensite begins upon cooling for a nickel-titanium shape memory alloy, and martensite finish temperature ($M_f$) refers to the temperature at which the phase transformation to martensite concludes. Austenite start temperature ($A_s$) refers to the temperature at which a phase transformation to austenite begins upon heating for a nickel-titanium shape memory alloy, and austenite finish temperature ($A_f$) refers to the temperature at which the phase transformation to austenite concludes.

Figure 1A:
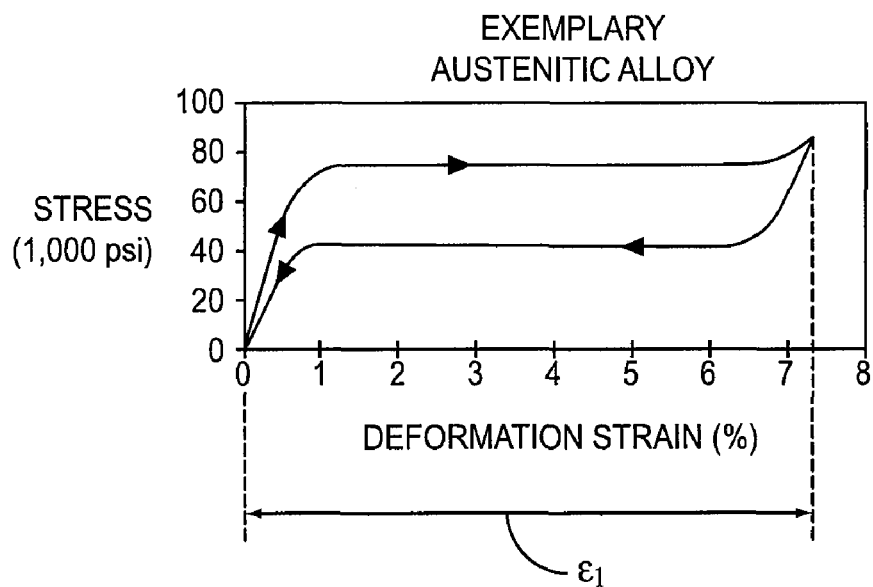
FIG. 1A shows a stress-strain diagram for an exemplary shape memory nickel-titanium alloy at a temperature at or above an austenitic final temperature ($A_f$) of the alloy.
Figure 1B:
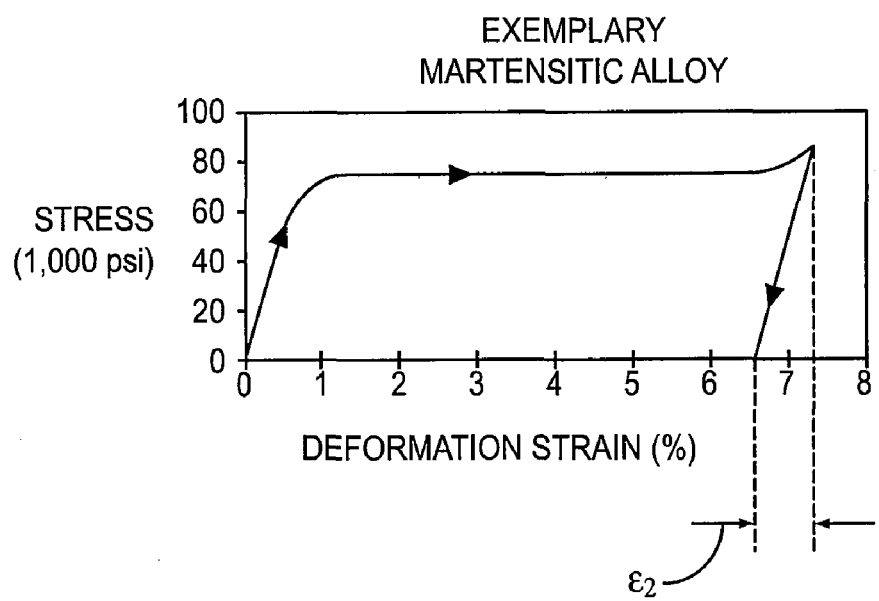
FIG. 1B shows a stress-strain diagram for an exemplary martensitic shape memory nickel-titanium alloy at a temperature below an austenitic start temperature ($A_s$) of the alloy.
Figure 2A:
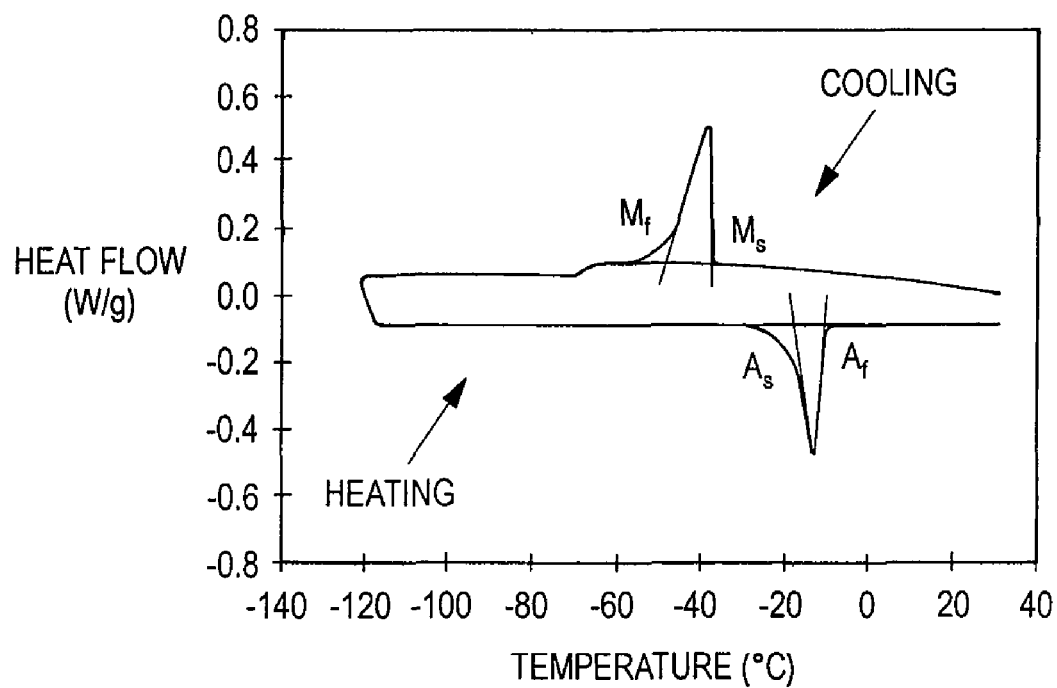
FIG. 2A is a differential scanning calorimetry (DSC) curve obtained for an exemplary nickel-titanium shape memory alloy exhibiting a single-stage transformation.

FIG. 2A shows differential scanning calorimetry (DSC) data for an exemplary nickel-titanium shape memory alloy that undergoes a single-stage transformation involving the austenitic and martensitic phases. The exemplary DSC data shown in the figure are based on those published in the ASTM standard F2005-05 and are not intended to be limiting. DSC data show the heat absorbed or released by a specimen as a function of temperature, and thus allow phase transformation temperatures to be identified. As shown, the relationship of the phase transformation temperatures for the exemplary shape memory alloy shown in FIG. 2A is $M_f < M_s < A_s < A_f$.

Some nickel-titanium shape memory alloys may exhibit a two-stage transformation which includes a transformation to a rhombohedral phase (R-phase) in addition to the monoclinic (B12) martensitic phase and the cubic (B2) austenitic phase. The transformation to R-phase in two-stage shape memory materials occurs prior to the martensitic transformation upon cooling and prior to the austenitic transformation upon heating.

Figure 2B:
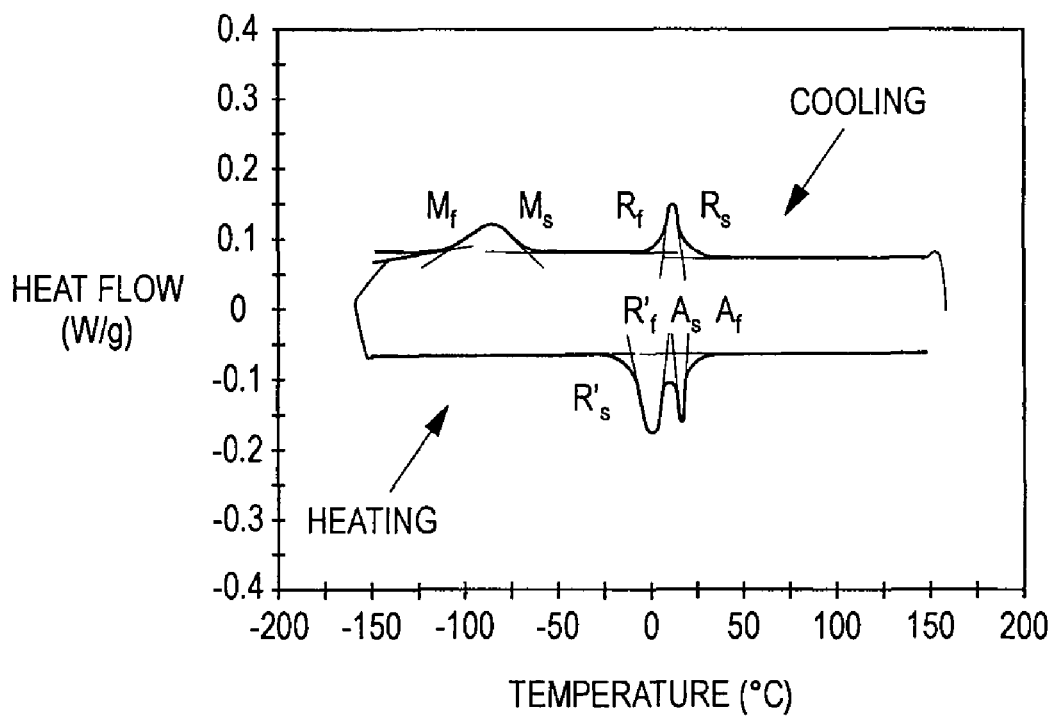
FIG. 2B is a differential scanning calorimetry (DSC) curve obtained for an exemplary nickel-titanium shape memory alloy exhibiting a two-stage transformation.

FIG. 2B shows a DSC plot of an exemplary shape memory alloy that undergoes a two-stage transformation. FIG. 2B is based on data published in the ASTM standard F2005-05 and is intended to be exemplary but not limiting. Referring to the figure, R'-phase start temperature ($R'_s$) is the temperature at which a phase transformation to R-phase begins upon heating for the two-stage shape memory material, and R'-phase finish temperature ($R'_f$) is the temperature at which the phase transformation to R-phase concludes upon heating. Note that, upon heating, the shape memory material may consist partly of the R-phase and partly of martensite from the R'-phase start temperature $R'_s$ until the R'-phase finish temperature $R'_f$, and then entirely of the R-phase from $R'_f$ until $A_s$ is reached, at which point the austenitic phase begins to form in the alloy. At or above $A_s$, the alloy may consist partly of R-phase and partly of austenite until $A_f$ is reached, at which point the alloy is entirely austenitic. This discussion assumes the warming of the shape memory alloy occurs without an applied stress. If stress is applied to the alloy, the R-phase may remain stable at temperatures at or above $A_f$.

Again referring to FIG. 2B, R-phase start temperature ($R_s$) refers to the temperature at which a phase transformation to R-phase begins upon cooling for a two-stage shape memory material, and R-phase finish temperature ($R_f$) refers to the temperature at which the phase transformation to R-phase concludes upon cooling. Note that, upon cooling, the shape memory alloy may consist partly of the R-phase and partly of austenite from the R-phase start temperature $R_s$ until a temperature of $R_f$, and then entirely of the R-phase from $R_f$ until $M_s$ is reached, at which point the martensitic phase begins to form in the alloy. At or below a temperature of $M_s$, the alloy may consist partly of R-phase and partly of martensite until $M_f$ is reached, at which point the alloy is entirely martensitic. This discussion assumes the cooling of the shape memory alloy occurs without an applied stress. If stress is applied to the alloy, the R-phase may appear at a temperature above $R_s$, and the R-phase transformation may conclude at a temperature above $R_f$.

Consequently, for the purposes of this disclosure, an R-phase temperature range may generally be defined as a range of temperatures over which the R-phase may be present in the shape memory alloy. For example, during heating, the R-phase temperature range may extend from at or above R', to below $A_f$ of the shape memory alloy, assuming zero stress conditions. If stress is applied to the alloy, the R-phase may be stable at temperatures at or above $A_f$. In another example, during cooling, the R-phase temperature range may extend from at or below $R_s$ to above $M_f$ of the shape memory alloy, assuming zero stress conditions. If stress is applied to the alloy, the R-phase may appear at a temperature above R, and the R-phase transformation may conclude at a temperature above $R_f$.

Loading Method

Figure 3A:
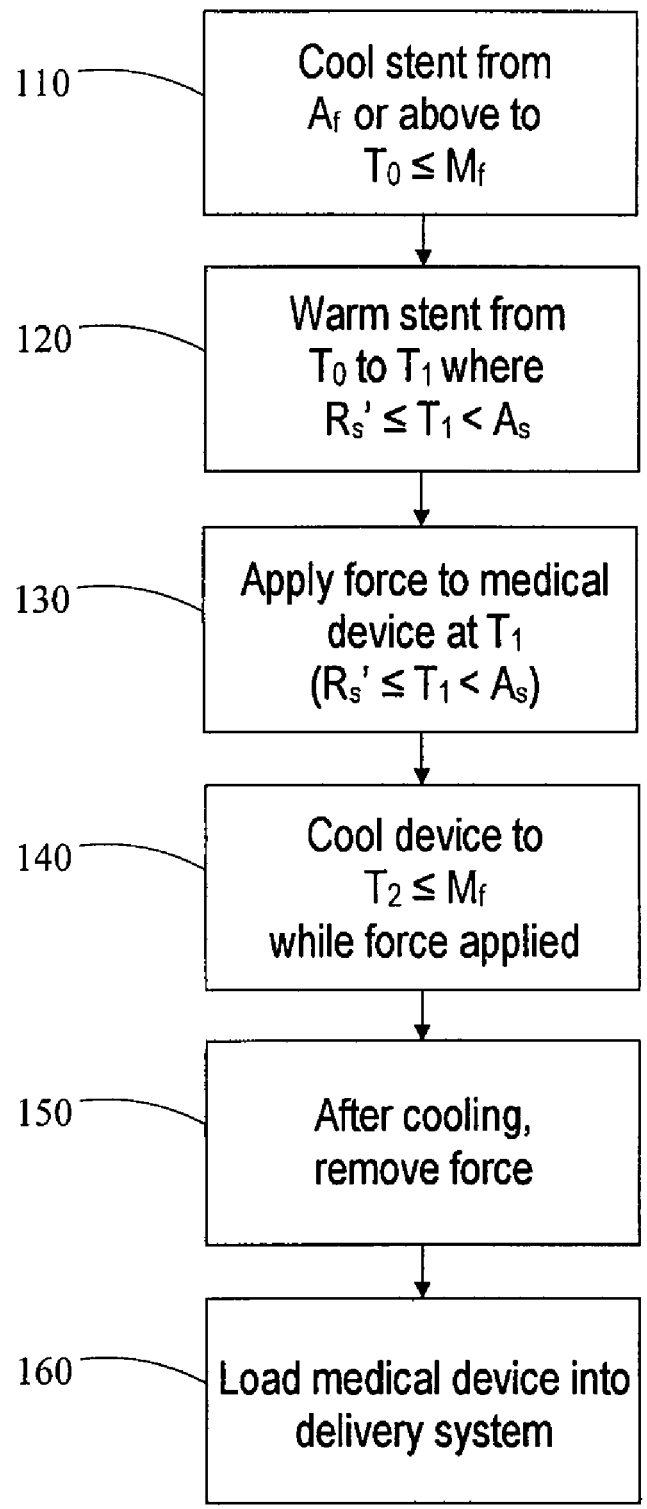
FIG. 3A is a flow diagram showing the steps of preparing a medical device for loading into a delivery system, according to a preferred procedure.
Figure 3B:
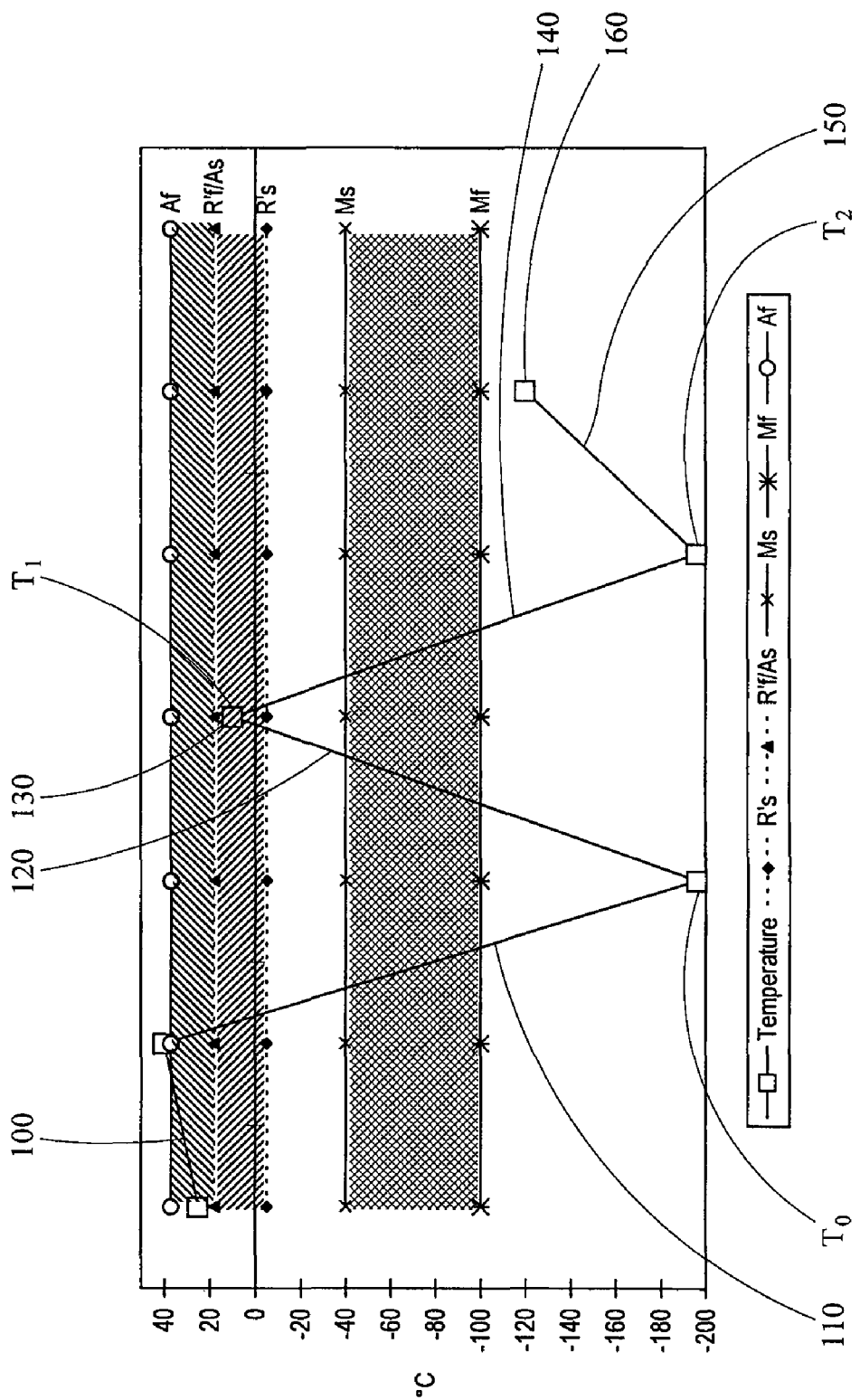
FIG. 3B is a schematic showing the temperature cycles involved in preparing a medical device for loading into a delivery system, according to the preferred procedure shown in FIG. 3A.

FIGS. 3A and 3B show the steps and temperature cycles of a preferred loading method for a self-expanding stent comprising a shape memory material. Initially, the stent is at or above the austenite finish temperature $A_f$ of the shape memory material. For example, a stent having transformation temperatures within the ranges shown in Table 1 may be inserted into a controlled environment maintained at 40° C. (>$A_f$) and allowed to equilibrate within the controlled environment. As discussed in the preceding section, at or above the austenite finish temperature $A_f$ of the shape memory material, the stent may have a fully austenitic structure.

After reaching the temperature of the controlled environment, the stent may be cooled 110 to an initial temperature $T_0$ that is preferably at or below the martensite finish temperature $M_f$ of the shape memory material. For example, the stent may be transferred to a second controlled environment and cooled by immersion in a liquid nitrogen bath. Liquid nitrogen has a temperature of about −196° C., which is below the martensite finish temperature $M_f$ of the exemplary shape memory material whose transformation temperatures are given in Table 1. Accordingly, the stent may attain a fully martensitic structure upon cooling to the initial temperature $T_0$. Preferably, the second controlled environment may be maintained at a temperature below the austenite start temperature $A_s$ of the shape memory material of the stent to avoid a phase transformation to austenite upon removal of the stent from the liquid nitrogen bath. For example, the second controlled environment may be maintained at a temperature of about 10° C. in the case of the exemplary shape memory material of Table 1.

TABLE 1

| Transformation Temperature | Range (° C.) for Exemplary Shape Memory Material |
|---|---|
| $A_f$ | 30 to 37 |
| $A_s$ | 15 to 20 |
| $R_s$ | 15 to 20 |
| $R'_f$ | 10 to 15 |
| $R_f$ | 10 to 15 |
| $R'_s$ | −10 to 0 |
| $M_s$ | −80 to −30 |
| $M_f$ | −140 to −80 |

After cooling in the liquid nitrogen bath, the stent may be warmed 120 from the initial temperature $T_0$ a first temperature $T_1$ which is above $M_f$. Preferably, the first temperature $T_1$ lies at or above $R'_s$ but below $A_s$ of the shape memory material, as shown in FIG. 3B. It may be desirable to warm the stent to the top one-third of this temperature range. Within this range, the shape memory material of the stent may include both martensite and R-phase. The warming to the first temperature $T_1$ may entail removing the stent from the liquid nitrogen bath and allowing it to warm up to the temperature of the second controlled environment.

Once the stent has reached the first temperature $T_1$ a compressive force may be applied 130 to the stent to obtain a reduced diameter configuration (i.e., a delivery configuration) suitable for loading the stent into a transfer tube, sheath or other delivery vehicle. The compressive force may be applied by a compression unit. The compression unit may take the form of, for example, a stent rolling apparatus which includes a flexible sheet or foil rolled to define a cylindrical opening or aperture into which a stent may be inserted. By applying a force to an end of the sheet with the stent inside the opening, the diameter of the opening may be decreased and the stent may be radially compressed within the sheet. Preferably, the sheet is made of or coated with a material having a low coefficient of friction. The compression unit alternatively may take the form of a stent crimping apparatus that includes a plurality of contracting members disposed about a cylindrical aperture. The stent may be inserted into the aperture and then compressed as the relative motion of the contracting members reduces the size of the aperture. Such crimping machines are commercially available from various manufacturers, such as, for example, Machine Solutions, Inc. (Flagstaff, Ariz.). Alternatively, other compression units, bending machines, presses, forges, or other metalworking equipment known in the art may be used to apply the force to the stent.

Once compressed, the stent may be cooled 140 in the delivery configuration to a second temperature $T_2$ below the first temperature $T_1$. Preferably, the second temperature $T_2$ is at or below the martensite final temperature $M_f$. To carry out the cooling, the compressed stent may be reimmersed in the liquid nitrogen bath. Without wishing to be bound by theory, it is believed that this cooling step constitutes a "training" step for imparting a secondary shape memory that helps to minimize or prevent recoil (expansion) of the stent upon removal of the compressive force.

To halt the cooling, the stent may be removed from the liquid nitrogen bath. The compressive force may be released 150 from the stent, and the stent may be loaded 160 into a transfer tube, sheath or other delivery vehicle. Preferably, minimal recoil or expansion of the stent occurs following removal of the compressive force. Even more preferably, no expansion of the stent occurs following removal of the compressive force, for at least a period of 10-30 seconds. Consequently, the stent may be loaded into the tube with minimal or no discernible resistance. Preferably, the loading occurs immediately or within about 10-30 seconds after removing the compressive force. It is also desirable that the loading be carried out in the controlled environment maintained at a temperature below the austenite start temperature $A_s$ so that the stent does not undergo a phase transformation to austenite during loading.

After the time period of about 10-30 seconds, some expansion or recoil of the stent may occur. However, it is possible to halt the expansion and substantially recover the compressed configuration of the stent by recooling the stent in liquid nitrogen. The recooling may be most effective when the temperature of the stent, after removing the compressive force, has not risen beyond about the martensite finish or start temperatures, $M_f$ or $M_s$.

It is possible to measure the diameter of the stent during application of the force and after the force is removed to determine if any recoil or expansion of the stent has occurred. For example, when the stent is being compressed, software associated with the compression unit may be able to track and record the diameter of the stent, including the minimum diameter attained by the compression unit. A laser micrometer may then be employed to measure the diameter of the stent after the force is released and the cooling is ceased (e.g., after the stent is removed from the liquid nitrogen bath). To obtain such a measurement, the stent may be momentarily moved into the laser beam field. From these data, the amount of recoil, if any, may be determined.

The loading method is suitable for use with self-expanding stents of any size, and may be advantageously used with longer-length stents. The stent employed in the loading process may have any length suitable for expanding a constriction in a body vessel. For example, the method may facilitate the loading of stents of 80 mm or longer into transfer tubes or delivery sheaths with minimal frictional forces and without damage to the stent. Stents of 100 mm or longer may also be loaded using the present method. Alternatively, the loading method may also be used with stents of 80 mm or shorter in length.

The present loading method is also applicable to medical devices other than self-expanding stents. For example, the medical device may be a stone retrieval basket, a snare, or an embolic protection filter including one or more shape memory/superelastic components (e.g., wires). In another example, the medical device may be a superelastic fenestration ring which is used as a coupling device for a stent graft. The stent graft may include a self-expanding stent with a graft material attached to the stent.

Alternative versions of the loading method are envisioned, as described below.

Figure 4:
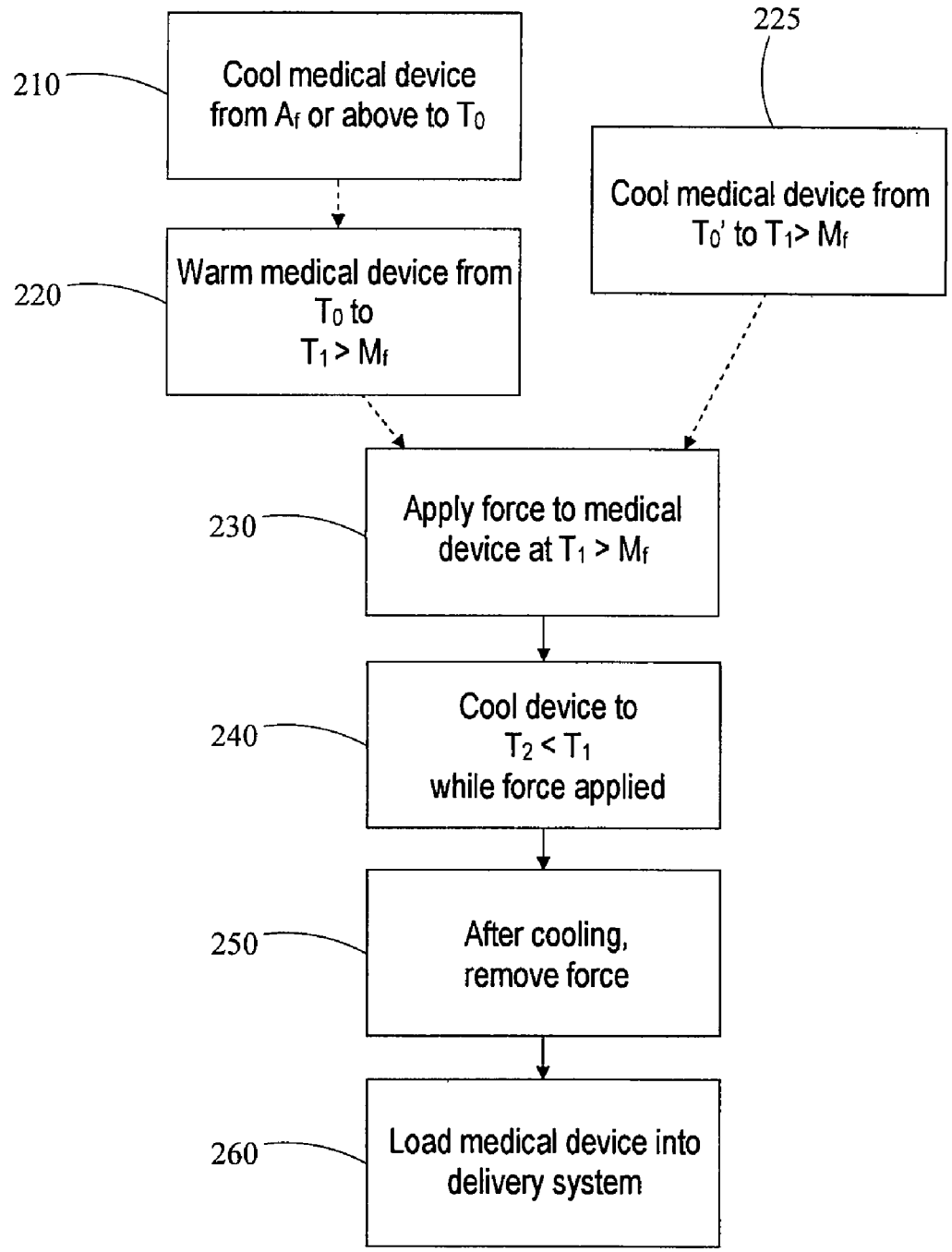
FIG. 4 is a flow diagram showing the steps of preparing a medical device for loading into a delivery system, according to an alternative procedure.

FIG. 4 shows a flow diagram for an alternative loading procedure. The procedure entails applying a force 230 to a medical device to obtain a delivery configuration of the medical device. When the force is applied 230, the device is at a first temperature ($T_1$) above a martensite finish temperature of the shape memory material. The medical device is then cooled 240 in the delivery configuration to a second temperature ($T_2$) below the first temperature. After cooling 240, the force is removed 250 from the medical device, and the device is loaded 260 into a delivery system. Preferably, the medical device substantially maintains the delivery configuration during the loading process. This procedure may be most suitable when minimizing the profile of the medical device is not of paramount importance.

The force applied 230 to the medical device to obtain the delivery configuration may be a compressive force. For example, a compressive radial force may be applied to a self-expanding stent made of a shape memory material to obtain a compressed configuration of the stent. The compressive force may be applied by a compression unit as described above.

Preferably, the first temperature $T_1$ at which the force is applied 230 is above the martensite finish temperature $M_f$ of the shape memory material. According to one aspect, the first temperature $T_1$ may be above the martensite start temperature $M_s$ of the shape memory material. The first temperature $T_1$ may also be at or above the R'-phase start temperature $R_s'$. It may be further advantageous for the first temperature $T_1$ to be below the austenite finish temperature $A_f$ of the shape memory material. For example, the first temperature $T_1$ may be below the austenite start temperature $A_s$ of the shape memory material. According to another aspect, the first temperature may be at or below the R'-phase finish temperature $R_f'$.

The loading method may include a step of warming 220 the medical device to the first temperature $T_1$ from an initial temperature $T_0$ prior to applying the force. Also, prior to reaching the initial temperature $T_0$, the medical device may be at or above the austenite finish temperature $A_f$ of the shape memory material. The device may thus be cooled 210 from a temperature at or above $A_f$ to the initial temperature $T_0$.

The initial temperature $T_0$ may be below the R'-phase start temperature $R_s'$ of the shape memory material, according to one aspect. Alternatively, the initial temperature $T_0$ may be at or below the martensite start temperature $M_s$ of the shape memory material. The initial temperature $T_0$ may also be at or below the martensite finish temperature $M_f$ of the shape memory material.

The warming 220 of the medical device from $T_0$ the first temperature $T_1$ may be carried out by exposing the medical device to a warm fluid, which may be a gas or a liquid or a combination of the two. For example, the medical device may be immersed in the warm fluid. Alternatively, the medical device may be exposed to a stream of the warm fluid. According to another aspect, the warming of the medical device may be carried out by removing the medical device from a cooling fluid and allowing the device to warm up by exposure to the specified temperature of the controlled environment. Alternatively, the medical device may be warmed by using a radiative heat lamp, an electrical resistance heater, or another heat source.

The warming 220 of the medical device to the first temperature $T_1$ may be carried out for a time sufficient to reach the first temperature. It is preferable that the warming be carried out for at least a few seconds. For example, the warming may be carried out for about 5 seconds or more. The warming may also be carried out for about five minutes or less. Preferably, the warming may be carried out for about 60 seconds or less. For example, the warming may be carried out for about 30 seconds or less. In another example, the warming may be carried out for about 15 seconds or less.

Alternatively, instead of warming 220 from an initial temperature $T_0$ the first temperature $T_1$, the medical device may be cooled 225 from a starting temperature $T_0'$ to the first temperature $T_1$ prior to applying the force. The starting temperature $T_0'$ may be above an R-phase start temperature $R_s$. The starting temperature $T_0'$ may also be at or above an austenite start temperature $A_s$ of the shape memory material. According to another aspect, the starting temperature may be at or above an austenite finish temperature $A_f$.

According to this aspect, the cooling 225 of the medical device to the first temperature $T_1$ may be carried out by exposing the medical device to a cold fluid, which may be a gas or a liquid or a combination of the two. For example, the medical device may be immersed in the cold fluid. Alternatively, the medical device may be exposed to a stream of the cold fluid. The cold fluid may be, for example, liquid nitrogen. According to another aspect, the medical device may be cooled by removing the medical device from a heat source and allowing it to cool by exposure to the specified temperature of the controlled environment.

The cooling 225 of the medical device to the first temperature $T_1$ may be carried out for a time sufficient to reach the first temperature $T_1$. It is preferable that the cooling may be carried out for at least a few seconds. For example, the cooling may be carried out for at least five seconds. According to another aspect, the cooling may be carried out for about five minutes or less. Preferably, the cooling may be carried out for about 60 seconds or less. For example, the cooling may be carried out for about 30 seconds or less. In another example, the cooling may be carried out for about 15 seconds or less.

After applying the force 230 to the medical device at the first temperature $T_1$ to obtain the delivery configuration as described above, the medical device may be cooled 240 in the delivery configuration to a second temperature $T_2$ below the first temperature $T_1$. According to one aspect, the second temperature $T_2$ may be lower than the R'-phase start temperature $R_s'$ of the shape memory material. The second temperature may also be at or below the martensite start temperature $M_s$ of the shape memory material. According to another aspect, the second temperature may be at or below the martensite finish temperature $M_f$ of the shape memory material. The cooling may be carried out as described above.

After the cooling 240 of the medical device in the delivery configuration, the force may be released 250 from the device. For example, the compressive radial force may be released from the self-expanding stent, and the stent may be removed from the compression unit.

The medical device may then be loaded 260 into a delivery system. According to one aspect, the stent may be loaded into a tube, such as a transfer tube, delivery sheath or the like. During the loading process, the delivery system (e.g., tube) may be held in place manually or by a fixation device. According to one aspect, the delivery system may have a temperature of less than the $A_f$ of the shape memory material of the medical device. According to another aspect, the delivery system may have a temperature of less than the $A_s$ of the shape memory material of the medical device.

It may also be advantageous to carry out the loading method in an enclosed environment maintained at a specified temperature. The specified temperature may be ambient temperature, according to one aspect. According to another aspect, the specified temperature may be less than the austenite finish temperature $A_f$ of the shape memory material. Preferably, the specified temperature is less than the austenite start temperature $A_s$ of the shape memory material.

Preferably, the medical device substantially maintains the delivery configuration for at least as long as the duration of the loading process 260. For example, the medical device may substantially maintain the delivery configuration for at least about 10 seconds following removal of the force, or for at least about 20 seconds after removing the force. Preferably, the medical device substantially remains in the delivery configuration for at least about 30 seconds following removal of the force. Accordingly, loading the medical device into the tube may require an axial force of about 1 N or less. For example, the force may be about 0.5 N or less. In another example, the force may be about 0.1 N or less. The axial loading force may be measured by a load cell.

Figure 5:
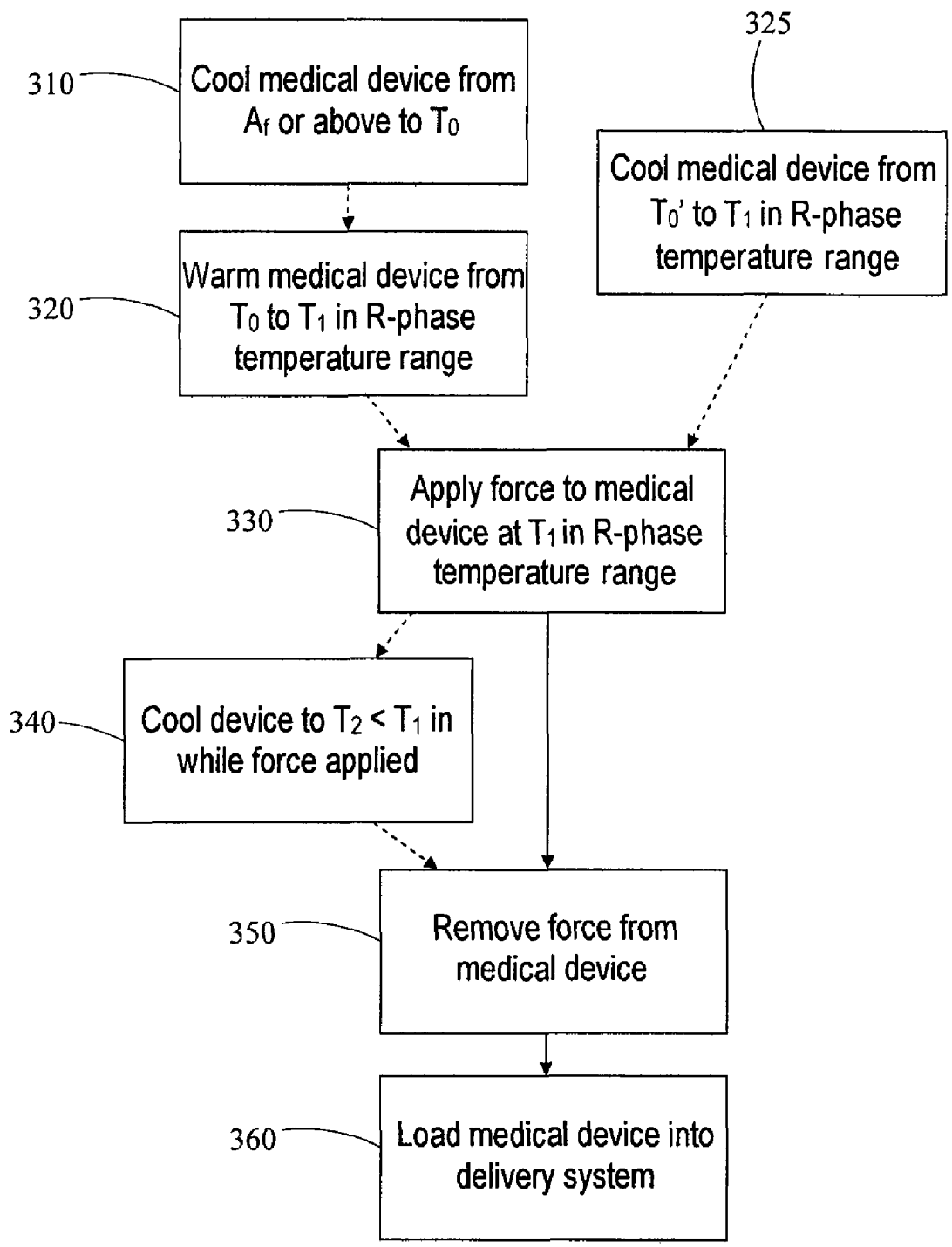
FIG. 5 is a flow diagram showing the steps of preparing a medical device for loading into a delivery system, according to an alternative procedure.

FIG. 5 shows a flow diagram illustrating another loading procedure. Referring to the figure, the loading method includes applying a force 330 to a medical device comprising a shape memory material to obtain a delivery configuration of the medical device. Preferably, the medical device is at a first temperature $T_1$ within an R-phase temperature range of the shape memory material during application of the force 330. The force is then removed 350 from the medical device, and the device is loaded 360 into a delivery system. Preferably, the medical device substantially maintains the delivery configuration at least during the loading process.

The medical device may be warmed 320 from an initial temperature $T_0$ to the first temperature $T_1$ in the R-phase temperature range prior to applying the force. The initial temperature $T_0$ may be below the R'-phase start temperature of the shape memory material. According to another aspect, the initial temperature $T_0$ may be at or below the martensite start temperature $M_s$ of the shape memory material. Alternatively, the initial temperature $T_0$ may be at or below the martensite finish temperature $M_f$ of the shape memory material. The warming 320 of the medical device from the initial temperature $T_0$ the first temperature $T_1$ within the R-phase temperature range may be carried out as described previously.

Prior to reaching the initial temperature $T_0$, according to one aspect, the medical device may be at or above the austenite finish temperature $A_f$ of the shape memory material. The device may thus be cooled 310 from a temperature at or above $A_f$ to the initial temperature $T_0$.

If the medical device is warmed 320 to the first temperature $T_1$ in the R-phase temperature range, the R-phase temperature range may extend from the R'-phase start temperature $R_s'$ to below the austenite finish temperature $A_f$ of the shape memory material. The R-phase temperature range may alternatively range from the R'-phase start temperature $R_s'$ to below the austenite start temperature $A_s$ of the shape memory material. According to another aspect, the R-phase temperature range may range from the R'-phase start temperature $R_s'$ to the R'-phase finish temperature $R_f'$.

Alternatively, instead of being warmed 320 from an initial temperature $T_0$ the first temperature $T_1$ in the R-phase temperature range, the medical device may be cooled 325 to the first temperature $T_1$ from a starting temperature $T_0'$. The starting temperature $T_0'$ may be above the R-phase start temperature $R_s$ of the shape memory material, or the starting temperature $T_0'$ may be at or above the austenite start temperature $A_s$. According to another aspect, the starting temperature $T_0'$ may be at or above the austenitic final temperature $A_f$. The cooling 325 of the medical device from $T_0'$ to the first temperature $T_1$ may be carried out as described previously.

As explained above, the boundaries of the R-phase temperature range depend on whether or not the shape memory material is being heated or cooled. Consequently, in the case of cooling to the first temperature $T_1$ in the R-phase temperature range, the R-phase temperature range may extend from the R-phase start temperature $R_s$ to above the martensite finish temperature $M_f$. The R-phase temperature range may alternatively range from the R-phase start temperature $R_s$ to above the martensite start temperature $M_s$. Alternatively, the R-phase temperature range may range from the R-phase start temperature $R_s$ to the R-phase finish temperature $R_f$.

Preferably, the force applied to the medical device to obtain the delivery configuration is a compressive force. The force may be applied to the medical device as described previously.

Before removing the force from the medical device, the medical device may be cooled 340 to a second temperature $T_2$ below the first temperature $T_1$ in the R-phase temperature range, according to one aspect of the method. The second temperature $T_2$ may be lower than the R'-phase start temperature $R_s'$ of the shape memory material, or the second temperature may be at or below the martensite start temperature $M_s$ of the shape memory material. Alternatively, the second temperature may be at or below the martensite finish temperature $M_f$ of the shape memory material. The cooling 340 may be carried out as described previously.

The force may be removed 350 from the medical device, and the medical device may be loaded into a delivery system. For example, a compressive radial force applied by a compression unit may be released and a stent may be removed from the unit for loading 360 into a transfer tube or a sheath. During the loading process, the delivery system (e.g., tube) may be held in place manually or by a fixation device. The delivery system may have a temperature of less than the austenite finish temperature $A_f$ of the shape memory material of the medical device. Preferably, the delivery system has a temperature of less than the austenite start temperature $A_s$ of the shape memory material of the medical device.

It may also be advantageous to carry out the loading method in an enclosed environment maintained at a specified temperature. The specified temperature may be ambient temperature, or the specified temperature may be less than the austenite finish temperature $A_f$ of the shape memory material. Preferably, the specified temperature is less than the austenite start temperature $A_s$ of the shape memory material.

Preferably, the medical device maintains the delivery configuration for at least as long as the duration of the loading process 360. For example, the medical device may maintain the delivery configuration for at least about 5 seconds following removal of the force. According to one aspect, the medical device maintains the delivery configuration for at least about 10 seconds following removal of the force. According to another aspect, the medical device remains in the delivery configuration for at least about 20 seconds after removing the radial force. Preferably, the medical device remains in the delivery configuration for at least about 30 seconds following removal of the radial force. Accordingly, loading the medical device into the tube may require an axial force of about 1 N or less. For example, the force may be about 0.5 N or less. In another example, the force may be about 0.1 N or less. The axial loading force may be measured by a load cell.

Secondary Shape Memory Training Method

Figure 6:
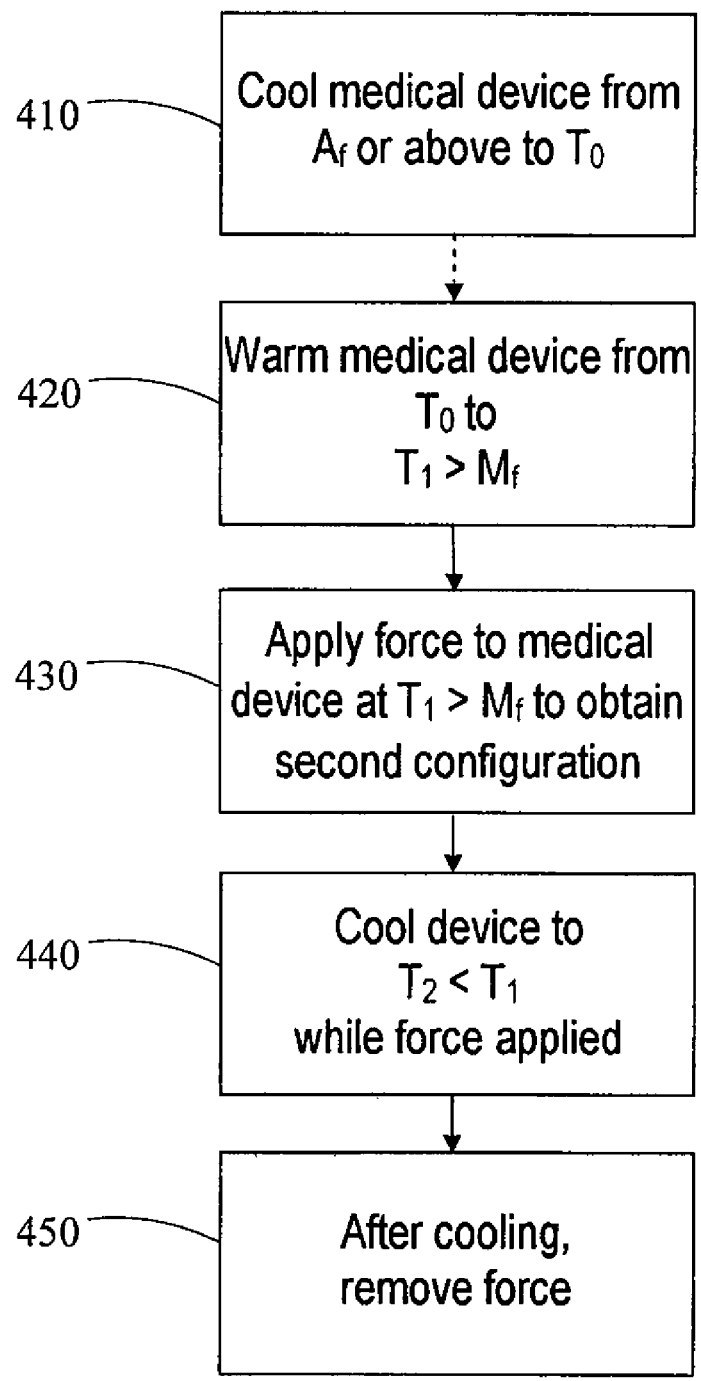
FIG. 6 is a flow diagram showing the steps of training a component to have a secondary shape memory.

A secondary shape memory training method for a medical device comprising a shape memory material is also described herein. The method involves providing a medical device comprising a shape memory material and imparting a secondary shape memory to the material. Above an austenite finish temperature $A_f$ of the shape memory material, the device comprises a first configuration. A preferred aspect of the training method is illustrated in the flow diagram of FIG. 6. The method includes warming 420 the medical device to a first temperature $T_1$ above the martensite finish temperature $M_f$ of the shape memory material from an initial temperature $T_0$. A force is then applied 430 to the medical device at the first temperature $T_1$ to obtain a second configuration. The medical device is cooled 440 in the second configuration to a second temperature $T_2$ below the first temperature $T_1$. Without wishing to be bound by theory, this step is believed to constitute a "training" step for imparting the secondary shape memory. After the cooling, the force is removed 450 from the medical device. Upon recooling to the second temperature $T_2$, the medical device substantially returns to the second configuration.

The medical device may be at or above the austenite finish temperature $A_f$ of the shape memory material prior to reaching the initial temperature $T_0$. The device may thus be cooled 410 from a temperature at or above $A_f$ to the initial temperature $T_0$.

The initial temperature $T_0$ may be below the R'-phase start temperature $R_s'$ of the shape memory material, according to one aspect of the method. Alternatively, the initial temperature $T_0$ may be at or below the martensite start temperature $M_s$ of the shape memory material. Preferably, the initial temperature $T_0$ is at or below the martensite finish temperature $M_f$ of the shape memory material.

The warming 420 of the medical device from the initial temperature $T_0$ to the first temperature $T_1$ may be carried out as described previously.

According to one aspect, the force applied 430 to the medical device made of the shape memory material to obtain the second configuration of the medical device may be a compressive force. For example, a compressive radial force may be applied to a self-expanding stent made of a shape memory material to obtain a compressed configuration of the stent. The compressive radial force may be applied by a compression unit as described previously. Alternatively, bending machines, presses, forges, or other metalworking equipment known in the art may be used to apply the force to the medical device.

Preferably, the medical device is at the first temperature $T_1$ above the martensite finish temperature $M_f$ of the shape memory material during the application 430 of the force. The first temperature $T_1$ may be above the martensite start temperature $M_f$ of the shape memory material. Alternatively, the first temperature $T_1$ may be at or above the R'-phase start temperature $R_s'$ of the shape memory material. It may also be advantageous that the first temperature $T_1$ is below the austenite finish temperature $A_f$ of the shape memory material. For example, the first temperature may be below the austenite start temperature $A_s$. Alternatively, the first temperature $T_1$ may be at or below the R-phase start temperature $R_s$ of the shape memory material.

After applying force 430 to the medical device at the first temperature $T_1$, the medical device may be cooled 440 in the second configuration to a second temperature $T_2$ below the first temperature $T_1$. According to one aspect of the method, the second temperature $T_2$ may be lower than the R'-phase start temperature $R_s'$ of the shape memory material. According to yet another aspect, the second temperature $T_2$ may be at or below the martensite start temperature $M_s$. Preferably, the second temperature $T_2$ is at or below the martensite finish temperature $M_f$. The cooling 440 may be carried out as described above.

After the cooling 440, the force may be removed 450 from the medical device. The medical device preferably maintains the second configuration following removal 450 of the force. The medical device may begin to warm up. After warming for a sufficient time and/or upon reaching a given temperature, the medical device may begin to "recoil" or recover the first configuration from the second configuration. Ultimately, upon warming to a temperature at or above an austenite finish temperature $A_f$, the medical device may fully recover the first configuration due to a phase change to austenite. Upon recooling to the second temperature $T_2$ (or below), however, the medical device may substantially recover or return to the second configuration. How effectively the shape memory material recovers the second configuration upon recooling may depend on the temperature to which the medical device warms before recooling. Preferably, the medical device warms to a temperature of no more than the martensitic start temperature $M_s$ of the shape memory material. More preferably, the device warms to a temperature of no more than the martensite finish temperature $M_f$. For example, the device may reach a temperature of no more than about 100° C. above the second temperature $T_2$. Alternatively, the device may warm to a temperature of no more than about 50° C. above the second temperature $T_2$.

The medical device may recover at least about 75% of the second configuration relative to the first configuration upon recooling to the second temperature $T_2$. For example, if the medical device is a stent, the second configuration may be a radially compressed state of about 2 mm in diameter compared to a radially expanded state of about 10 mm in diameter in the first configuration. In this example, the stent may return to a diameter of about 4 mm or less upon recooling to the second temperature $T_2$. Preferably, the medical device attains at least about 90% of the second configuration relative to the first configuration. For example, the aforementioned stent may preferably return to a diameter of about 2.8 mm or less upon recooling to the second temperature or below. More preferably, the medical device attains at least about 95% of the second configuration relative to the first configuration. For example, the stent may return to a diameter of about 2.4 mm or less upon recooling to the second temperature or below. Most preferably, the medical device attains 100% of the second configuration relative to the first configuration. For example, the stent may return to a diameter of about 2.0 mm upon recooling to the second temperature or below. Accordingly, the medical device may exhibit a two-way shape memory effect in which the second configuration is "remembered" and substantially recovered at lower temperatures.

It may be possible to determine the recovery percentage of the stent or other medical device by measuring the diameter of the stent during application of the force and after recooling. For example, when the stent is being compressed, software associated with the compression unit may be able to track and record the diameter of the stent, including the minimum diameter attained by the compression unit. A laser micrometer may then be employed as described earlier to measure the diameter of the stent after the force is released and the cooling is ceased, as well as after recooling. From these data, the extent of the recovery of the second configuration may be determined.

According to one aspect, the warming 420 of the medical device to the first temperature $T_1$, the application of force 430 to the device, the cooling 440 of the device to the second temperature, and the removal of force 450 from the device constitute a single secondary shape memory training cycle. It may be advantageous to carry out more than one training cycle to improve the two-way shape memory effect, e.g., to improve the percentage of the second configuration that may be recovered upon recooling. By carrying out more than one training cycle, it may also be possible to increase the amount of time after the force is removed before the medical device begins to return to the first configuration.

For example, two training cycles may be carried out. Alternatively, a plurality of training cycles may be desirable. For example, at least three training cycles may be carried out. In another example, at least five training cycles may be carried out. In yet another example, it may be advantageous to carry out at least ten training cycles.

It may be advantageous to carry out the secondary shape memory training method in an enclosed environment maintained at a specified temperature. The specified temperature may be ambient temperature, according to one aspect. Alternatively, the specified temperature may be less than the austenite finish temperature $A_f$ of the shape memory material. Preferably, the specified temperature is less than the austenite start temperature $A_s$ of the shape memory material.

Shape Memory Material

The shape memory material employed in the loading and secondary (or two-way) shape memory training methods described herein may be a nickel-titanium shape memory material (e.g., Nitinol). The nickel-titanium alloy may have a near-equiatomic composition. Preferably, the nickel-titanium alloy is a two-stage shape memory material that undergoes an R-phase transformation. Such materials may be obtained from commercial sources or fabricated as described herein.

To produce a nickel-titanium shape memory alloy, the desired amounts of nickel and titanium may be melted and then cooled into an ingot or a workpiece. Melting methods known in the art, including but not limited to vacuum induction melting (VIM), vacuum consumable arc melting (VAR), and electron beam melting, may be employed to form the melt. Remelting is generally desirable to obtain satisfactory microstructural homogeneity in the ingot. For example, successive VAR processes or a VIM/VAR double melting process may be employed.

To ensure that the nickel-titanium alloy undergoes an R-phase transformation, it may be advantageous to select a nickel-rich composition, such as, for example, about 51 at. % Ni and 49 at. % Ti, for the melt. According to another aspect, one or more additional alloying elements (e.g., ternary or quaternary elements) may be included in the alloy composition. It may also be advantageous to cold work and then anneal the alloy at a temperature of between about 400° C. and 550° C., as will be described below. Each of these steps may help to suppress the martensitic phase transformation relative to the R-phase transformation.

The ingot formed from the melting process may be hot worked into a first shape by, for example, extruding, hot rolling, or forging. Hot working may be employed to break down the cast structure of the ingot and to improve mechanical properties. The hot working may be carried out at temperatures in the range of from about 700° C. to about 950° C. Preferably, the ingot undergoes a minimum deformation of about 90% during hot working in order to obtain a uniform microstructure.

The first shape may then be cold worked into a component by, for example, drawing or rolling. The cold working typically involves several passes in combination with interpass annealing treatments at temperatures in the range of from about 600° C. to about 800° C. The interpass annealing treatments soften the material between cold work passes, which typically impart 30-40% deformation to the material. Machining operations, such as, for example, drilling, cylindrical centerless grinding, or laser cutting may also be employed to fabricate the component.

A heat treatment may be employed to impart a "memory" (primary shape memory) of a desired high temperature shape and to optimize the shape memory/superelastic and mechanical properties of the component. The number, duration and the temperature of the heat treatments may affect the transformation temperatures. Typically, heat treatment temperatures of 400° C. to 550° C. are appropriate to set the final shape and optimize the shape memory and mechanical properties.

Determination of Phase Transformation Temperatures

The transformation temperatures $M_f$, $M_s$, $R_s'$, $R_f'$, $R_f$, $R_s$, $A_s$, and $A_f$ of the shape memory alloy may be determined using differential scanning calorimetry (DSC) techniques known in the art. DSC measurements may be carried out according to the American Society for Testing and Materials (ASTM) standard F2004-05 entitled "Standard Test Method for Transformation Temperature of Nickel-Titanium Alloys by Thermal Analysis," which is hereby incorporated by reference. Alternatively, methods known as constant load dilatometry and bend and free recovery may be employed to determine the transformation temperatures. Bend and free recovery tests may be carried out in accordance with the ASTM standard F2082-03 entitled "Standard Test Method for Determination of Transformation Temperature of Nickel-Titanium Shape Memory Alloys by Bend and Free Recovery," which is hereby incorporated by reference. Electrical resistivity measurements are also known in the art for determining the phase transformation temperatures of metals and alloys. Such measurements may be carried out by heating and cooling the alloy of interest while recording voltage using a four-probe constant current technique, for example. Using electrical resistivity measurements, it is possible to characterize phase transformations occurring in the nickel-titanium alloy as a function of applied stress as well as temperature. Diffraction methods, including x-ray, electron and/or neutron diffraction, may also be employed to evaluate the crystal structure of the materials as a function of temperature.

Improved Phase Transformation Characterization Method

In some cases, DSC testing as provided by the ASTM Standard F2004-05 may be insufficient to fully characterize the phase transformations of shape memory alloys exhibiting an R-phase transformation. For some shape memory alloys, two distinct exothermic peaks are obtained in the data during cooling (the first corresponding to the austenite to R-phase transformation and the second corresponding to the R-phase to martensite transformation), but only a single endothermic valley is obtained during heating. This valley is generally believed to be formed by two overlapping sub-valleys (the first corresponding to the martensite to R-phase transformation and the second corresponding to the R-phase to austenite transformation). However, using the standard DSC test method, it is not possible to isolate and define these overlapped sub-valleys. Accordingly, phase transformation temperatures, in particular $R'_f$ and $A_s$, can only be estimated.

An improved method of characterizing phase transformations in shape memory alloys comprising an R-phase transformation is described in a related patent document, U.S. patent application Ser. No. 60/992,258 entitled "Method of Characterizing Phase Transformations in Shape Memory Materials," which was filed on Dec. 4, 2007, and is hereby incorporated by reference in its entirety. The improved method allows overlapping inflections (e.g., valleys) in DSC or other data to be deconvoluted into sub-inflections (e.g., sub-valleys) that represent distinct phase transformations. Accordingly, the method may allow phase transformation temperatures, such as $A_s$ and $R'_f$, to be unambiguously determined for shape memory alloys having an R-phase transformation.

According to one embodiment of the improved method, a shape memory alloy specimen having an R-phase transformation is placed in a device configured to record data during heating and cooling. Preferably, the device is a differential scanning calorimeter and the data recorded are heat flow as a function of temperature. The specimen is cooled to a first temperature sufficient to define a first inflection and a second inflection in the data. The first inflection occurs over a first temperature interval and corresponds to a phase transformation from austenite to R-phase, and the second inflection occurs over a second temperature interval and corresponds to a phase transformation from R-phase to martensite. The specimen is then heated to a second temperature sufficient to define a third inflection in the data. Preferably, the specimen is substantially fully austenitic at the second temperature. The third inflection occurs over a third temperature interval and is formed by overlapping first and second sub-inflections corresponding, respectively, to phase transformations from martensite to R-phase and from R-phase to austenite. Cooling to the first temperature and heating to the second temperature constitute the first loop of the DSC experiment. The specimen is then cooled to a third temperature between the first inflection and the second inflection, whereby the shape memory alloy has a substantially fully R-phase structure, and the specimen is heated to a fourth temperature sufficient to define the second sub-inflection in the data corresponding to the phase transformation from R-phase to austenite. Cooling to the third temperature and heating to the fourth temperature constitute the second loop of the DSC experiment. Data are recorded throughout the test. This improved testing method may be referred to as a "double-loop" experiment.

By carrying out the double-loop experiment, it is possible to isolate the second sub-valley corresponding to the R-phase to austenite phase transformation from the overlapped valley obtained during a single DSC loop. Using these DSC data, it is further possible to computationally define the first sub-valley of the overlapped valley corresponding to the martensite to R-phase transformation.

One computational approach to defining the first sub-valley corresponding to the martensite to R-phase transformation is direct mathematical subtraction. As described above, the double loop experiment allows the second sub-valley to be isolated from the overlapped valley formed upon heating. The data corresponding to the overlapped valley and the second sub-valley is exported out of the DSC software program in an x and y format. Since both the overlapped valley and the second sub-valley have common x (temperature) values, direct subtraction may be used to determine the y (enthalpy) values for the first sub-valley.

The mathematical equations may take the form of:

$$X_{(A+R')} = X_A$$

$$Y_{(A+R')} - Y_A = Y_{R'}$$

where $X_{(A+R')}$ and $X_A$ represent the x values of the overlapped valley and the second sub-valley, respectively, and $Y_{(A+R')}$, $Y_A$, and $Y_{R'}$ represent the y values of the overlapped valley, the second sub-valley and the first sub-valley, respectively. Using the calculated and normalized $Y_{R'}$ (enthalpy) values, the first sub-valley may then be plotted as a function of x (temperature) along with the experimentally-determined overlapped valley and the second sub-valley.

A tangent technique may be employed to determine the phase transformation temperatures of the shape memory alloy, which generally correspond to the lower and upper boundaries of each peak or valley. ASTM Standard 2004-05 prescribes drawing the tangents through the inflection points of the peaks or valleys, and obtaining the transformation temperatures (e.g., $M_s$ and $M_f$) as the graphical intersection of the baseline of the DSC data with the extension of the line of maximum inclination. This approach is illustrated in FIGS. 2A and 2B. Other tangent line determination approaches may be suitable for particularly broad peaks, where passing the tangent line through the inflection point of the peak or valley skews the results. Software programs, such as TA Instruments' Universal Analysis software, include tangent line determination routines for automatic generation of tangent lines and phase transformation temperatures.

Thus, by combining the experimental double-loop method with computational analysis, an overlapped valley may be unambiguously separated into its component first and second sub-valleys. Accordingly, phase transformations for a shape memory alloy exhibiting an R-phase transformation may be properly characterized, and phase transformation temperatures (e.g., $R'_s$, $R'_f$, $A_s$ and $A_f$) may be accurately determined.

EXAMPLE 1

A self-expanding stent comprising a nickel-titanium shape memory alloy having transformation temperatures within the ranges given in Table 1 is loaded into a transfer tube. The steps of the exemplary loading process described in this example are shown schematically in FIG. 3B.

First, the stent is heated 100 to a temperature at or above the austenite finish temperature $A_f$ of the shape memory alloy. After equilibrating in an environment maintained at a temperature of about 40° C., which is above $A_f$, the stent is transported to an enclosed environment ("cold box") maintained at a temperature of about 10° C. The stent is then immersed in liquid nitrogen having a temperature of about –196° C. for several seconds to cool 110 the stent and induce a phase transformation to martensite. The immersion is carried out in a liquid-nitrogen filled container having dimensions large enough to completely submerge the stent. Additional liquid nitrogen may flow into the container periodically through a line connected to a liquid nitrogen source to replenish the supply of fluid. In this way, a steady level of liquid nitrogen is maintained in the container.

After being immersed in liquid nitrogen and cooled 110 to a temperature below the martensite finish temperature $M_f$ of the shape memory alloy, the stent is placed in a holder within the cold box for approximately a few minutes to one hour to warm up 120 and equilibrate with the cold box temperature of about 10° C. At this temperature, which is above the R'-phase start temperature $R'_s$ of the shape memory alloy, it is expected that the structure of the stent includes both martensite and R-phase.

While at the temperature of 10° C., the stent is loaded into a compression unit disposed within the cold box. The compression unit may be a stent rolling apparatus that includes a flexible sheet rolled to define an opening or an aperture into which a stent can be inserted, as described previously. With the stent disposed in the opening of the rolling apparatus, a force is applied 130 to an end of the sheet to decrease the diameter of the opening, and the stent is radially compressed within the sheet to obtain a compressed configuration of the stent.

Within a few seconds of initiating the compression, the stent is immersed in the liquid nitrogen-filled container described above and cooled 140 to a temperature of about –196° C., which is below the martensite finish temperature $M_f$ of the shape memory alloy. The compression 130 of the stent continues for about 30 seconds while the stent is immersed in liquid nitrogen.

Finally, the stent is removed 150 from the liquid nitrogen to halt the cooling, and the compressive force is released from the stent. The stent is removed from the stent rolling apparatus and loaded 160 into a transfer tube having a temperature equilibrated with the cold box temperature. The stent is loaded into the tube with no discernible resistance during the loading process. The loading occurs within a time period of about 10 seconds following removal of the compressive force.

EXAMPLE 2

Self-expanding stents comprising a nickel-titanium shape memory alloy having the transformation temperatures given in Table 2 are loaded into transfer tubes in a series of tests (Experiments 1.1 to 3.2) described below. The results of the tests are summarized in Table 3.

TABLE 2

| Transformation Temperature | Approximate Value for Stents of Example 2 (° C.) |
| --- | --- |
| $A_f$ | 29 |
| $A_s$ | 20 |
| $R_s$ | 26.5 |
| $R'_f$ | ~20-30 |
| $R_f$ | 15 |
| $R'_s$ | 2.5 |
| $M_s$ | –34 |
| $M_f$ | –85 |

In the experiments, each stent is heated or cooled to a temperature within a specified R-phase temperature range, and then compressed as described in Example 1 at that temperature. The structure of each stent is thus partially or fully R-phase prior to compression. The impact of the training step (cooling prior to release of the compressive force) on the loading process is explored in the experiments.

Experiment 1.1
Stent Warmed to $R'_s$>T>$R'_f$ for Compression

For this experiment, the loading procedure is carried out as follows. First, the stent is immersed in liquid nitrogen until the stent attains a temperature of about –196° C. Next, the stent is allowed to warm up to a temperature of greater than $R'_s$ of the shape memory alloy but less than $R'_f$. Within this temperature regime, it is expected that stent includes both martensite and R-phase. The stent is then compressed using approximately 10 lbs of force. During the compression, the stent is dipped in liquid nitrogen for about 40 seconds. The stent is removed from the liquid nitrogen and the force is released. Finally, the stent is loaded into a tube having an internal diameter of 1.65 mm. The experiment is carried out using two different stents, each measuring 7 mm (expanded diameter)×140 mm (length).

During the loading procedure using the first stent (#151123-2), the cold box is maintained at a temperature of about 7.3° C. A thermocouple positioned near to the compression region registers a temperature of 3.7° C. The diameter of the compressed stent is measured to be about 1.49 mm at the start of the compression, and the diameter decreases slightly to about 1.47 mm when the stent is immersed in liquid nitrogen while still under the 10 lbs of force. After release of the force, the stent can be loaded into the 1.65 mm-diameter tube without resistance.

During the loading procedure using the second stent (#151123-4), the cold box is maintained at a temperature of about 7.3° C. A thermocouple positioned near to the compression region registers a temperature of 3.8° C. The diameter of the compressed stent is measured to be about 1.50 mm at the start of the compression, and the diameter decreases slightly to about 1.45 mm when the stent is immersed in liquid nitrogen while still under the 10 lbs of force. After release of the force, the stent can be loaded into the 1.65 mm-diameter tube without resistance.

Experiment 1.2
Stent Warmed to $R'_s$>T>$R'_f$ for Compression
No Cooling Before Force is Removed In this example, two different stents are loaded into a tube according to the procedure described in Experiment 1.1, except that the stents are not immersed in liquid nitrogen before the compressive force is removed.

During the loading procedure using the first stent (#151123-3), the cold box temperature is maintained at a temperature of about 8.8° C. A thermocouple positioned near to the compression region reads a temperature of about 3.6° C. The diameter of the compressed stent is measured to be about 1.49 mm. After release of the compressive force, the stent recoils (expands) almost immediately to a diameter of about 3.99 mm as determined using calipers. As a result, the stent cannot be loaded into the 1.65 mm-diameter tube without resistance. However, the stent remains at the 3.99 mm diameter (approximately 57% of the fully expanded diameter) for a time (e.g., minutes) more than sufficient to load the stent into a larger-diameter tube.

During the loading procedure using the second stent (#151123-5), the cold box temperature is maintained at a temperature of about 8.5° C. A thermocouple positioned near to the compression region reads a temperature of about 5.0° C. The diameter of the compressed stent is measured to be about 1.48 mm. When the compressive force is released from the stent, the stent immediately recoils (expands) to approximately 50% of its fully expanded diameter, or about 3.56 mm. Accordingly, loading of the stent into the 1.65 mm-diameter tube is not attempted. However, the stent remains at the 3.56 mm diameter for a time (e.g., minutes) more than sufficient to load the stent into a larger-diameter tube.

Experiment 2.1
Stent Cooled to $M_s<T<R_f$ for Compression

For this experiment, the loading procedure is carried out as follows. First, the stent is cooled from room temperature to a temperature of greater than $M_s$ of the shape memory alloy but less than $R_f$. Within this temperature regime, it is expected that the stent has a fully R-phase structure. The stent is then compressed using approximately 10 lbs of force. During the compression, the stent is dipped in liquid nitrogen for about 40 seconds. The stent is removed from the liquid nitrogen and the force is released. Finally, the stent is loaded into a tube having an internal diameter of 1.65 mm. The experiment is carried out using two different stents, each measuring 7 mm (expanded diameter)×140 mm (length).

During the loading procedure using the first stent (#151123-6), the cold box is maintained at a temperature of about 4.6° C. A thermocouple positioned near to the compression region registers a temperature of 1.4° C. The diameter of the compressed stent is measured to be about 1.50 mm at the start of the compression, and the diameter decreases slightly to about 1.45 mm when the stent is immersed in liquid nitrogen while still under the 10 lbs of force. After release of the force, the stent can be loaded into the 1.65 mm-diameter tube without resistance.

During the loading procedure using the second stent (#151123-7), the cold box is maintained at a temperature of about 5.4° C. A thermocouple positioned near to the compression region registers a temperature of 1.9° C. The diameter of the compressed stent is measured to be about 1.36 mm at the start of the compression, and the diameter decreases slightly to about 1.34 mm when the stent is immersed in liquid nitrogen while still under the 10 lbs of force. After release of the force, the stent can be loaded into the 1.65 mm-diameter tube without resistance.

Experiment 2.2
Stent Cooled to $M_s<T<R_f$ for Compression
No Cooling Before Force is Removed In this example, two different stents each measuring 8 mm (expanded diameter)×140 mm (length) are loaded into a tube according to the procedure described in Experiment 2.1, except that the stents are not immersed in liquid nitrogen before the compressive force is removed.

During the loading procedure using the first stent (#151600-1), the cold box temperature is maintained at a temperature of about 4.9° C. A thermocouple positioned near to the compression region reads a temperature of about 0.9° C. The diameter of the compressed stent is measured to be about 1.35 mm. After release of the compressive force, the stent recoils (expands) almost immediately to a diameter of about 3.25 mm as determined using calipers. As a result, loading of the stent into the 1.65 mm-diameter tube is not attempted. However, the stent substantially remains at the 3.25 mm diameter (approximately 41% of the fully expanded diameter) for a time (e.g., minutes) more than sufficient to load the stent into a larger-diameter tube.

During the loading procedure using the second stent (#151600-2), the cold box temperature is maintained at a temperature of about 6.7° C. A thermocouple positioned near to the compression region reads a temperature of about 4.5° C. The diameter of the compressed stent is measured to be about 1.38 mm. When the compressive force is released from the stent, the stent immediately recoils (expands) to approximately 44% of its fully expanded diameter, or about 3.49 mm. Accordingly, loading of the stent into the 1.65 mm-diameter tube is not attempted. However, the stent substantially remains at the 3.49 mm diameter for a time (e.g., minutes) more than sufficient to load the stent into a larger-diameter tube.

Experiment 3.1
Stent Cooled to $R_f<T<R_s$ for Compression

For this experiment, the loading procedure is carried out as follows. First, the stent is cooled from room temperature to a temperature of greater than $R_f$ of the shape memory alloy but less than $R_s$. Within this temperature regime, it is expected that stent has a partially R-phase and partially austenitic structure. The stent is then compressed using approximately 10 lbs of force. During the compression, the stent is dipped in liquid nitrogen for about 40 seconds. The stent is removed from the liquid nitrogen and the force is released. Finally, the stent is loaded into a tube having an internal diameter of 1.65 mm. The experiment is conducted using two different stents, each measuring 8 mm (expanded diameter)×140 mm (length).

During the loading procedure using the first stent (#151608-1), the cold box is maintained at a temperature of about 20.8° C. A thermocouple positioned near to the compression region registers a temperature of 16.6° C. The diameter of the compressed stent is measured to be about 1.35 mm at the start of the compression, and the diameter decreases slightly to about 1.28 mm when the stent is immersed in liquid nitrogen while still under the 10 lbs of force. After release of the force, the stent can be loaded into the 1.65 mm-diameter tube without resistance.

During the loading procedure using the second stent (#151608-2), the cold box is maintained at a temperature of about 21.3° C. A thermocouple positioned near to the compression region registers a temperature of 18.6° C. The diameter of the compressed stent is measured to be about 1.37 mm at the start of the compression, and the diameter decreases slightly to about 1.31 mm when the stent is immersed in liquid nitrogen while still under the 10 lbs of force. After release of the force, the stent can be loaded into the 1.65 mm-diameter tube without resistance.

Experiment 3.2
Stent Cooled to $R_f<T<R_s$ for Compression
No Cooling Before Force is Removed In this example, two different stents each measuring 8 mm (expanded diameter)×140 mm (length) are loaded into a tube according to the procedure described in Experiment 3.1, except that the stents are not immersed in liquid nitrogen before the compressive force is removed.

During the loading procedure using the first stent (#151608-3), the cold box temperature is maintained at a temperature of about 21.7° C. A thermocouple positioned near to the compression region reads a temperature of about 20.3° C. The diameter of the compressed stent is measured to be about 1.36 mm. After release of the compressive force, the stent recoils (expands) almost immediately to a diameter of about 7.16 mm as determined using calipers. This is approximately 90% of its expanded diameter. As a result, loading of the stent into the 1.65 mm-diameter tube is not attempted.

During the loading procedure using the second stent (#151608-4), the cold box temperature is maintained at a temperature of about 20.6° C. A thermocouple positioned near to the compression region reads a temperature of about 17.9° C. The diameter of the compressed stent is measured to be about 1.38 mm. When the compressive force is released from the stent, the stent immediately recoils (expands) to approximately 65% of its fully expanded diameter, or about 5.20 mm. Accordingly, loading of the stent into the 1.65 mm-diameter tube is not attempted.

TABLE 3

Summary of Data from Experiments of EXAMPLE 2

| Stent | Expanded Diameter (mm) | Phases at Compression Temperature | Cooling Before Force Removed? | Substantially Maintains Compressed State After Force Removed? |
|---|---|---|---|---|
| 151123-2 | 7 | R-phase and martensite | yes | Yes, stent loaded successfully |
| 151123-4 | 7 | R-phase and martensite | yes | Yes, stent loaded successfully |
| 151123-3 | 7 | R-phase and martensite | no | No, recoiled to ~57% of expanded diameter |
| 151123-5 | 7 | R-phase and martensite | no | No, recoiled to ~50% of expanded diameter |
| 151123-6 | 7 | R-phase | yes | Yes, stent loaded successfully |
| 151123-7 | 7 | R-phase | yes | Yes, stent loaded successfully |
| 151600-1 | 8 | R-phase | no | No, recoiled to ~41% of expanded diameter |
| 151600-2 | 8 | R-phase | no | No, recoiled to ~44% of expanded diameter |
| 151608-1 | 8 | R-phase and austenite | yes | Yes, stent loaded successfully |
| 151608-2 | 8 | R-phase and austenite | yes | Yes, stent loaded successfully |
| 151608-3 | 8 | R-phase and austenite | no | No, recoiled to ~90% of expanded diameter |
| 151608-4 | 8 | R-phase and austenite | no | No, recoiled to ~65% of expanded diameter |

A method to load a medical device, such as a stent, into a delivery system has been described. Preferably, the method permits the medical device to be loaded into the delivery system with minimal frictional forces during loading and without damage to the medical device. The process may be particularly advantageous for longer-length stents, which may buckle or collapse during conventional loading processes.

A method of training a medical device comprising a shape memory material to exhibit a secondary shape memory has also been described. The method may permit a medical device to recover a delivery configuration upon cooling.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A process for loading a medical device into a delivery system prior to insertion into a body lumen, the process comprising:
    applying a force to a medical device comprising a shape memory material to obtain a delivery configuration of the medical device, the medical device being at a first temperature within an R-phase temperature range of the shape memory material during the applying;
    removing the force from the medical device; and
    after removing the force, loading the medical device into a delivery system.

2. The process according to claim 1, further comprising cooling the medical device in the delivery configuration to a second temperature below the first temperature prior to removing the force from the medical device.

3. The process according to claim 2, wherein the second temperature is at or below a martensite finish temperature of the shape memory material.

4. The process according to claim 2, wherein the medical device recovers at least a portion of the delivery configuration upon recooling to the second temperature following removal of the force.

5. The process according to claim 1, wherein the medical device substantially maintains the delivery configuration for a time of at least about 5 seconds following removal of the force.

6. The process according to claim 1, wherein the loading is carried out in an environment maintained at a temperature of less than an austenite start temperature of the shape memory material.

7. The process according to claim 1, further comprising warming the medical device from an initial temperature to the first temperature in the R-phase temperature range.

8. The process according to claim 7, wherein the R-phase temperature range extends from an R'-phase start temperature to below an austenite start temperature of the shape memory material.

9. The process according to claim 8, wherein the initial temperature is at or below a martensite finish temperature of the shape memory material.

10. The process according to claim 1, further comprising cooling the medical device from a starting temperature to the first temperature in the R-phase temperature range.

11. The process according to claim 10, wherein the R-phase temperature range extends from an R-phase start temperature to above a martensite start temperature of the shape memory alloy.

12. The process according to claim 11, wherein the starting temperature is at or above an austenite finish temperature of the shape memory material.

13. The process according to claim 1, wherein the medical device is a self-expanding stent,
    wherein the force is a compressive radial force,
    wherein the delivery configuration is a compressed configuration, and
    wherein the delivery system is a tube, and further comprising warming the stent from an initial temperature at or below a martensite finish temperature to the first temperature within the R-phase temperature range, and further comprising cooling the stent in the compressed configuration to a second temperature at or below a martensite finish temperature of the shape memory alloy prior to removing the compressive radial force from the stent.

14. The process according to claim 1, further comprising, after loading the medical device into the delivery system, inserting the medical device into a body lumen.

15. A process for loading a medical device into a delivery system, the process comprising:
applying a force to a medical device comprising a shape memory material to obtain a delivery configuration of the medical device, the medical device being at a first temperature within an R-phase temperature range of the shape memory material during the applying;
cooling the medical device in the delivery configuration to a second temperature at or below a martensite finish temperature of the shape memory material;
removing the force from the medical device following the cooling;
loading the medical device into a delivery system, wherein the medical device substantially maintains the delivery configuration during loading.

16. The process according to claim 15, further comprising warming the medical device from an initial temperature to the first temperature in the R-phase temperature range.

17. The process according to claim 16, wherein the R-phase temperature range extends from an R'-phase start temperature to below an austenite start temperature of the shape memory material.

18. The process according to claim 15, further comprising cooling the medical device from a starting temperature to the first temperature in the R-phase temperature range.

19. The process according to claim 18, wherein the R-phase temperature range extends from an R-phase start temperature to above a martensite start temperature of the shape memory alloy.

20. A process for a loading a stent into a delivery system, the process comprising:
cooling a stent comprising a shape memory material from a temperature at or above an austenite finish temperature of the shape memory material to an initial temperature at or below a martensite finish temperature of the shape memory material;
warming the stent from the initial temperature to a first temperature at or above an R'-phase start temperature and below an austenite start temperature of the shape memory material;
applying a force to the stent to obtain a compressed configuration of the stent, the stent being at the first temperature during the applying;
cooling the stent in the compressed configuration to a second temperature at or below the martensite finish temperature;
removing the force from the stent after the cooling in the compressed configuration; and
loading the stent into a delivery system after removing the force, wherein the stent substantially maintains the compressed configuration during loading.

21. The process according to claim 20, wherein loading the stent into the delivery system comprises a force of less than about 1 N.

* * * * *